United States Patent

Morita

(10) Patent No.: US 10,395,516 B2
(45) Date of Patent: Aug. 27, 2019

(54) SAFETY INSTRUMENTED CONTROL APPARATUS AND METHOD THEREOF, AND SAFETY INSTRUMENTED SYSTEM

(71) Applicant: YOKOGAWA ELECTRIC CORPORATION, Tokyo (JP)

(72) Inventor: Yoshie Morita, Tokyo (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 15/934,706

(22) Filed: Mar. 23, 2018

(65) Prior Publication Data

US 2018/0301020 A1    Oct. 18, 2018

(30) Foreign Application Priority Data

Apr. 14, 2017   (JP) ................. 2017-080651

(51) Int. Cl.
| | |
|---|---|
| G08B 29/12 | (2006.01) |
| G08B 17/117 | (2006.01) |
| G08B 21/12 | (2006.01) |
| G08B 29/18 | (2006.01) |
| G01N 33/00 | (2006.01) |

(52) U.S. Cl.
CPC ........... G08B 29/126 (2013.01); G01N 33/00 (2013.01); G08B 17/117 (2013.01); G08B 21/12 (2013.01); G08B 29/183 (2013.01)

(58) Field of Classification Search
CPC ... G08B 29/126; G08B 17/117; G08B 29/183
USPC ............................................... 340/628
See application file for complete search history.

(56) References Cited

U.S. PATENT DOCUMENTS

| | | | | |
|---|---|---|---|---|
| 4,524,243 A | * | 6/1985 | Shapiro ............ | G08B 21/0415 340/573.1 |
| 6,028,513 A | * | 2/2000 | Addy ................. | G08B 25/016 340/12.52 |
| 6,078,269 A | * | 6/2000 | Markwell ........... | G08B 17/11 340/517 |
| 6,097,289 A | * | 8/2000 | Li ..................... | G08B 3/10 340/326 |
| 7,102,529 B2 | * | 9/2006 | Whitney ............ | A62C 2/24 340/628 |

(Continued)

FOREIGN PATENT DOCUMENTS

| | | | |
|---|---|---|---|
| JP | 2015185017 | * | 9/2015 |
| JP | 2017-059115 A | | 3/2017 |
| WO | WO-2016120662 A1 | * | 8/2016 ............ G08B 17/10 |

Primary Examiner — Omar Casillashernandez
(74) Attorney, Agent, or Firm — Osha Liang LLP

(57) ABSTRACT

A safety instrumented control apparatus includes: a message transmitter that transmits an alarm message to a display apparatus on the basis of an output from a field device that continues to output an alarm on the basis of detection of an abnormal condition until a reset operation is performed; a storage that stores a group ID for identifying a group of the field devices; a reset manager that counts on a timer until a predetermined amount of time passes after the reset operation; and a diagnoser that, during the count of the timer for any of the field devices belonging to the group ID, adds display suppression information to the alarm message related to the field device belonging to the group ID.

13 Claims, 7 Drawing Sheets

(56) References Cited

U.S. PATENT DOCUMENTS

| | | | | |
|---|---|---|---|---|
| 7,696,891 B2* | 4/2010 | Whitney | ................ | A62C 99/00 |
| | | | | 340/628 |
| 8,334,785 B1* | 12/2012 | Zetts | ...................... | G08B 7/064 |
| | | | | 340/309.16 |
| 8,354,935 B2* | 1/2013 | Rauworth | ............ | G08B 29/181 |
| | | | | 340/522 |
| 8,493,203 B2* | 7/2013 | Egawa | ................... | G08B 17/00 |
| | | | | 340/501 |
| 2009/0109016 A1* | 4/2009 | Baker | ...................... | G08B 1/08 |
| | | | | 340/506 |
| 2017/0083036 A1* | 3/2017 | Sueki | ........................ | G05F 1/66 |

* cited by examiner

SAFETY INSTRUMENTED CONTROL APPARATUS AND METHOD THEREOF, AND SAFETY INSTRUMENTED SYSTEM

CROSS-REFERENCE TO RELATED APPLICATION

This application claims priority from Japanese Patent Application No. 2017-080651 filed with the Japan Patent Office on Apr. 14, 2017, the entire content of which is hereby incorporated by reference.

BACKGROUND

1. Technical Field

The present invention relates to a safety instrumented control apparatus and a method thereof, and a safety instrumented system.

2. Description of the Related Art

In plants, factories, and the like (hereinafter they may be collectively referred to simply as "plants"), a process control system that controls various state quantities (such as pressure, temperature, and flow rate) in an industrial process has conventionally been constructed to achieve highly automated operation. The process control system includes a control system such as a distributed control system (DCS) and a safety system such as a safety instrumented system (SIS) to perform sophisticated control while ensuring safety.

The safety instrumented system includes at least any of, for example, a gas detector, a flame detector, a heat detector, and a smoke detector (hereinafter collectively referred to as F & G (Fire and Gas) devices) that are used to monitor plants, buildings, and the like so as to manage safety of a monitoring target on the basis of an output of the F & G device. When a problem that may bring about a severe disaster such as overflow of a toxic chemical or an explosion occurs, the safety instrumented system detects an important problem related to safety in the plant. Furthermore, the safety instrumented system executes, for example, the closing of a valve, a shutdown of power to a field device, and the switching of a flow in the plant to stop the operation of the plant safely. The safety instrumented system is provided as a part of, or independently of, the process control system.

The typical safety instrumented system includes the F & G device that detects, for example, gas, a flame, heat, or smoke, and outputs an alarm in accordance with a measurement result or a detection result by the F & G device. Japanese Patent Application No. 2015-185017 discloses a safety instrumented system using the F & G device. For example, the safety instrumented system detects an abnormal condition in response to a measurement value of the F & G device exceeding a predetermined threshold, outputs an alarm to an operation monitoring terminal, and displays an alarm message on a display of the operation monitoring terminal. Furthermore, the safety instrumented system detects a trip in response to a measurement value of the F & G device satisfying a predetermined given condition, and executes a shutdown of the plant that stops the operation of the plant safely. These operations are achieved by an application program to be executed in the safety instrumented system.

The F & G device is configured in such a manner as to, once detecting an abnormal condition (for example, gas, a flame, heat, or smoke), continue to output an alarm value being a measurement value indicating the abnormal condition even after a cause of the abnormal condition is eliminated. This is because after the abnormal condition is solved, an operator of the plant needs to confirm safety and then clear the alarm with his/her intention. In order for the operator of the plant to reset an abnormal detection state of the F & G device after confirming the occurrence of an abnormal condition, the power supplied to the F & G device is temporarily shut off. Hence, in a method that is typically used in the safety instrumented system using the F & G device, a power supply to supply the power to the F & G device is temporarily turned off to reset the F & G device. For example, in a circuit of the typical safety instrumented system, a relay circuit is provided in the middle of a power line connected to supply the power from the power supply to the F & G device. The relay circuit interrupts the supply of power to the F & G device in response to an operation via an input device such as a switch that is connected to the relay circuit. Consequently, it is possible to reset the F & G device and clear the alarm with the intention of the operator of the plant.

Moreover, a technology in this field is also disclosed in, for example, U.S. Pat. No. 8,354,935B2.

SUMMARY

A safety instrumented control apparatus according to one or more embodiments includes: a message transmitter configured to transmit an alarm message to a display apparatus on the basis of an output from a field device that continues to output an alarm on the basis of detection of an abnormal condition until a reset operation is performed; a storage configured to store a group ID for identifying a group of the field devices; a reset manager (reset circuit) configured to count on a timer until a predetermined amount of time passes after the reset operation; and a diagnoser (diagnosing circuit) configured to, during the count of the timer for any of the field devices belonging to the group ID, add display suppression information to the alarm message related to the field device belonging to the group ID.

DETAILED DESCRIPTION

Figure 1:
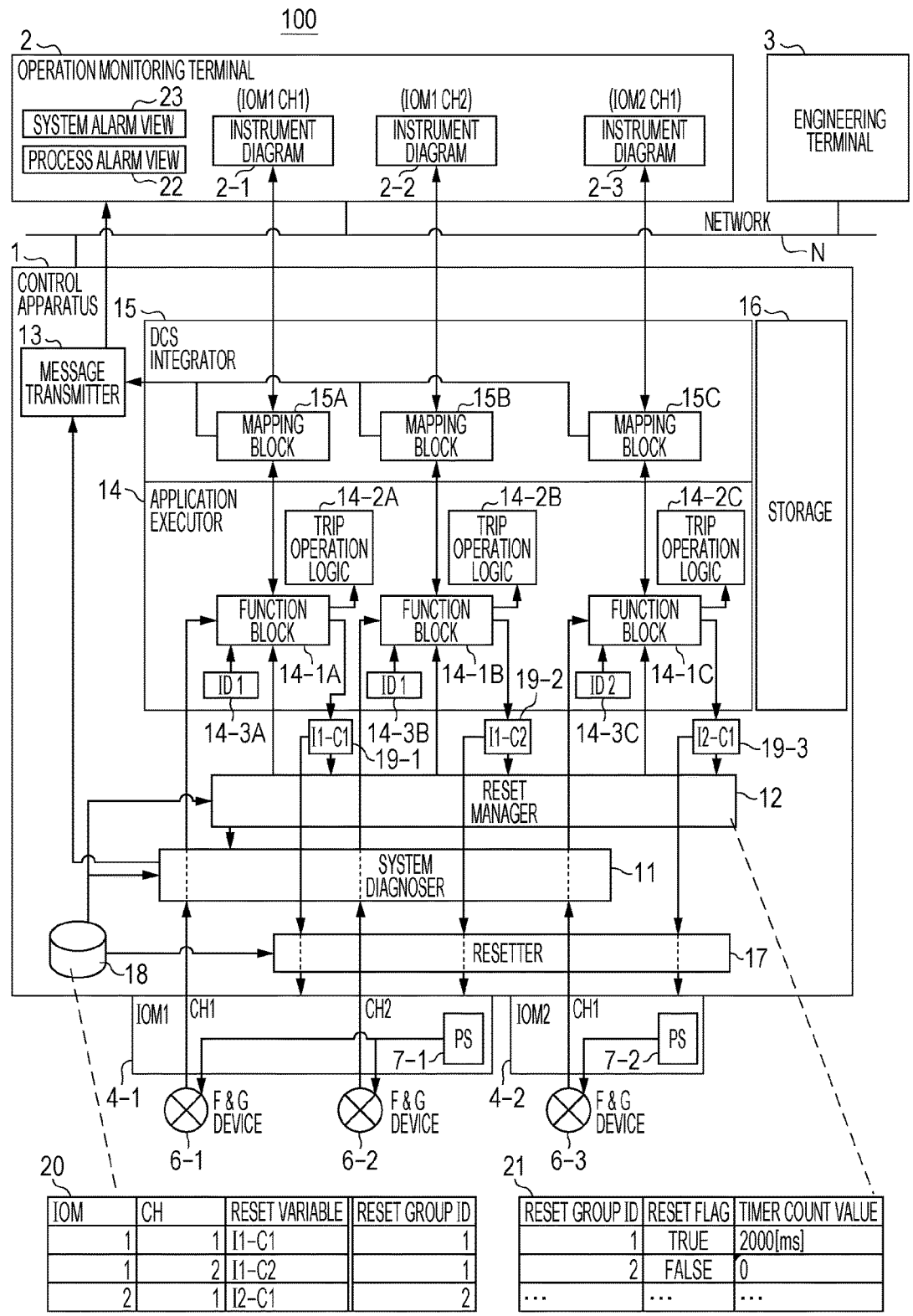
FIG. 1 is a configuration diagram of a safety instrumented system according to one or more embodiments of the invention.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

A safety instrumented system has a function of detecting an abnormal condition of a system or process, and displaying an alarm message on a display of an operation monitoring terminal. For example, a break in a cable for input signals is detected as an abnormal condition of the system and/or an abnormal condition of the process. In this case, an alarm message to the effect that the break has occurred is displayed on the display of the operation monitoring terminal. An operator of a plant performs, for example, maintenance on the basis of the alarm message displayed on the display of the operation monitoring terminal.

The safety instrumented system detects an abnormal condition on the basis of an alarm value outputted by an F & G device included in the safety instrumented system, and displays an alarm message on the display of the operation monitoring terminal. The operator of the plant can check the alarm message through the display of the operation monitoring terminal. After the abnormal condition is solved, the operator of the plant confirms safety, and then clears an alarm with the intention of the operator of the plant. Hence, for example, a safety instrumented system that can reset an F & G device by a resetter (resetting circuit) or the like is used. The reset F & G device is reactivated after the elapse of a predetermined amount of time and returns to a normal operating state.

During a period of time from when the F & G device starts being reset to when being reactivated (hereinafter referred to as "during reset"), the F & G device outputs an undefined value different from an output in the normal operating state. Hence, the safety instrumented system detects the output of the undefined value as, for example, an abnormal condition of the system such as a break, or an abnormal condition of the process, and displays an alarm message on the operation monitoring terminal. The abnormal condition of the system is detected by a system diagnoser provided to a control apparatus configuring a plant control system. The abnormal condition of the process is detected by an application program (application logic) to be executed by the control apparatus. When the abnormal condition of the system or process has been detected, a predetermined alarm message is transmitted from the control apparatus to the operation monitoring terminal. The operation monitoring terminal displays the received alarm message on the display.

However, the alarm message displayed in this case is a message displayed by resetting the F & G device and therefore, strictly speaking, is not an alarm message indicating an abnormal condition of the system or process. Hence, the operator of the plant should not perform, for example, maintenance on a plant facility on the basis of this alarm message. In order to solve such a problem, a technology for suppressing the display of an alarm, which does not display an alarm message during reset of the F & G device on the display of the operation monitoring terminal, is used.

For example, logic that does not detect an alarm during reset is built in the application program to suppress the display of an alarm.

Some safety instrumented systems use an annunciator (a system that notifies the operator that the process has gone into an abnormal state, and a system that issues a signal for alerting the operator concurrently with display of an alarm on the display apparatus) as a substitute for a process alarm being an alarm for an abnormal condition of the process of the plant. In this case, an engineer provides an application program for operating the control apparatus as follows: in other words, according to this program, if the F & G device is during reset, the control apparatus does not detect an abnormal condition of the process and accordingly does not transmit a message from the annunciator to the operation monitoring terminal. On the other hand, if the F & G device is not during reset, the control apparatus transmits a message of the annunciator to the operation monitoring terminal in response to the detection of the process alarm.

However, in this case, the engineer needs to build logic that suppresses an alarm during reset whenever building a new application program in response to a control design or design change of a new plant. Hence, an additional system resource is consumed, and accordingly the number of engineering man-hours and costs are required.

Moreover, the safety instrumented system handles a system alarm being an alarm for notifying an abnormal condition of the safety instrumented system itself or a part thereof. The system alarm is detected by a system diagnoser provided to the safety instrumented system, as a function different from the above-mentioned application program. When an abnormal condition has been detected in the system itself or a part thereof, an alarm signal is transmitted from the system diagnoser to display an alarm message on the operation monitoring terminal However, while it is necessary to suppress the display of an alarm message on the display of the operation monitoring terminal, an alarm management function of the operation monitoring terminal needs to handle all system alarms for the purpose of, for example, an alarm analysis. The notification of the system alarm is related to certification of SIL2 forming the basis of the safety system. Hence, a method that controls the system diagnoser with the application program and stops the issuance of a system alarm is conceivable as a method for suppressing the display of a system alarm during reset. However, in this method, an alarm that should be transmitted to the operation monitoring terminal is not transmitted while the issuance of an alarm is being stopped. Hence, it becomes impossible for the alarm management function of the operation monitoring terminal to handle all system alarms to be issued. Therefore, this method is not employed. Hence, when the display of an alarm is suppressed during reset, instead of the system diagnoser, an annunciator that is usable in the application program issues a system alarm. Specifically, the following method is employed: it is configured in such a manner that the system diagnoser is preset so as to turn off the operation before the start of the control apparatus in order to suppress the system diagnoser from operating; during operation of the control apparatus, the application program detects an abnormal condition of the system to transmit an annunciator message to the operation monitoring terminal; and during reset of the F & G device, the application program suppresses the detection of an abnormal condition of the system to suppress the transmission of an annunciator message to the operation monitoring terminal.

In this manner, whenever a new application program whose control target is the F & G device is constructed in the safety instrumented system, application logic for suppressing a system alarm needs to be constructed. Hence, an additional system resource is consumed, and accordingly the number of engineering man-hours and costs are required. Moreover, the setting of turning off the operation of the system diagnoser is performed. Accordingly, a human error such as the omission of the setting may occur. Furthermore, the annunciator essentially displays a message related to an abnormal condition of the process. Furthermore, the annunciator message is displayed in a predetermined area on the display apparatus, which is provided to display an alarm message about the process, but is difficult to be displayed in a predetermined area on the display apparatus, which is provided to display a system alarm. Hence, the above method is insufficient as a measure.

Figure 2:
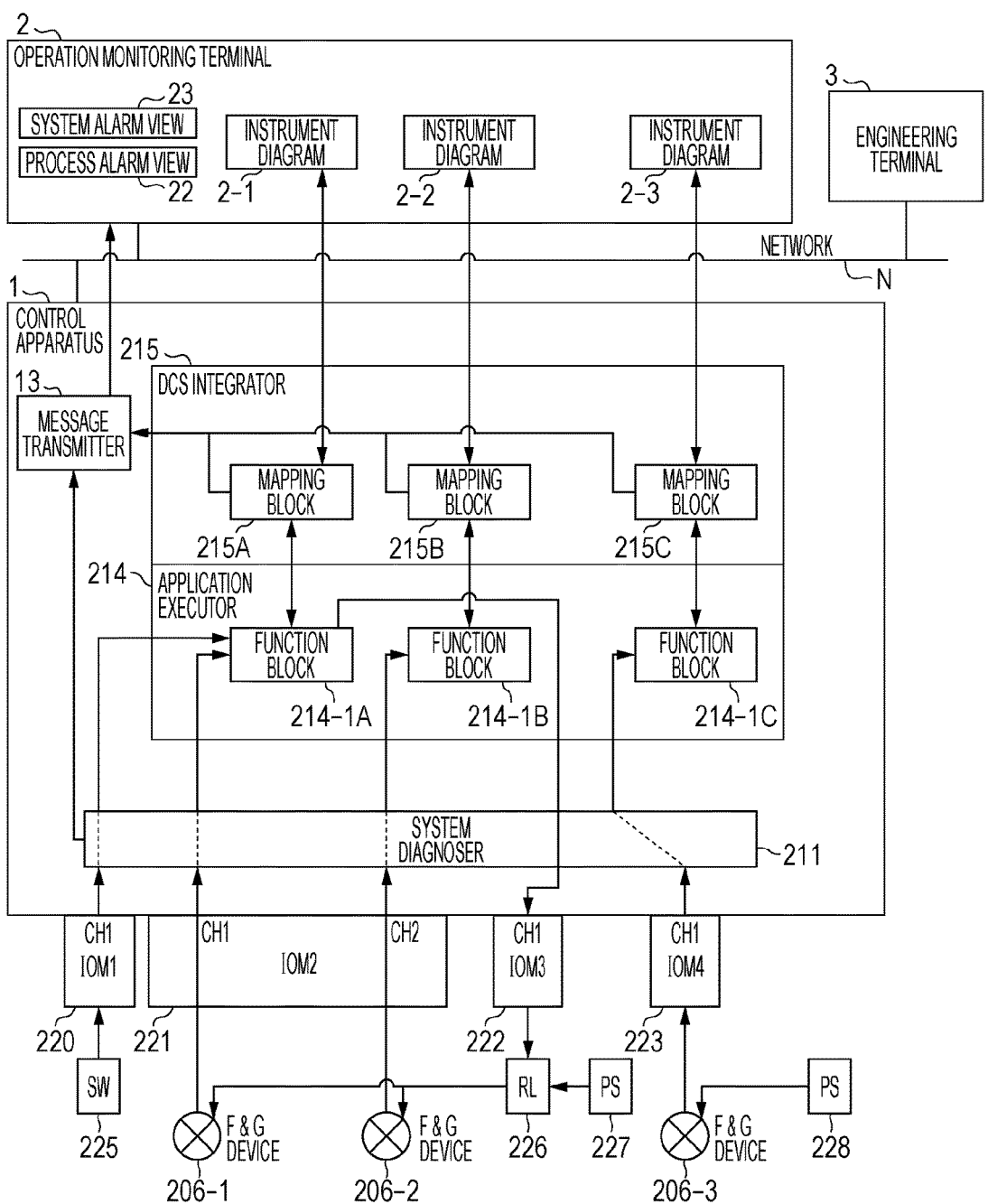
FIG. 2 is a configuration diagram describing the safety instrumented system according to one or more embodiments of the invention.

The reason that it is difficult to suppress the display of a system alarm during reset of the F & G device is described in more detail. FIG. 2 is a configuration diagram illustrating an example of the safety instrumented system. A safety instrumented system 200 is configured, mainly including a safety control apparatus 1 such as a safety controller, an operation monitoring terminal 2, input/output interfaces 220 to 223, F & G devices 206-1 to 206-3, a switch 225 for resetting the F & G devices 206-1 and 206-2, an external power supply 227 for supplying power to the F & G devices 206-1 to 206-2, a relay circuit 226 for shutting off the power to be supplied to the F & G devices 206-1 and 206-2, an external power supply 228 for supplying power to the F & G device 206-3, an application executer 214, and a process control system integrator 215.

Function blocks 214-1A, 214-1B, and 214-1C configure application logic to be executed by the application executer 214. The function blocks 214-1A, 214-1B, and 214-1C perform computations, control, and the like in a controller to control field devices (including the F & G devices). In FIG. 2, the function blocks 214-1A, 214-1B, and 214-1C have a function of diagnosing a process of a plant on the basis of data outputted from the F & G devices 206-1 to 206-3, and detecting a process alarm. Mapping blocks 215A, 215B, and 215C are a part of the process control system integrator 215 that logically couple a safety control system and the process control system. In FIG. 2, the mapping blocks 215A, 215B, and 215C transmit alarm signals of the process detected by the function blocks 214-1A, 214-1B, and 214-1C via a message transmitter 13 to the operation monitoring terminal 2 being a part of the process control system.

When the reset switch 225 has been pressed down, a reset signal is inputted into the function block 214-1A via the input/output interface 220. The function block 214-1A outputs a reset signal on the basis of the inputted reset signal. The reset signal is outputted to the relay circuit 226 via the input/output interface 222. The F & G devices 206-1 and 206-2 receive the supply of power from the power supply (PS) 227. When the reset signal has been inputted into the relay circuit (RL) 226, the relay circuit 226 temporarily interrupts the supply of power to the F & G devices 206-1 and 206-2. As a result, the F & G devices 206-1 and 206-2 are reset.

The F & G device 206-1 is connected to the function block 214-1A via a system diagnoser 211 through a channel CH1 of the input/output interface 221. The F & G device 206-2 is connected to the function block 214-1B via the system diagnoser 211 through a channel CH2 of the input/output interface 221. Therefore, when the F & G devices 206-1 and 206-2 are reset and then output undefined values different from measurement values in their normal operating states during reset, the system diagnoser 211 transmits an alarm signal of a system alarm for the channel CH1 of an input/output module IOM2 and the channel CH2 of the input/output module IOM2 to the operation monitoring terminal 2 via the message transmitter 13. Moreover, an undefined value different from a measurement value of the normal operating state, the undefined value resulting from the reset, is not outputted from the F & G device 206-3 that has not been reset. Hence, the system diagnoser 211 does not transmit an alarm signal of the system resulting from the undefined value for a channel CH1 of an input/output module IOM4. Moreover, the function blocks 214-1A and 214-1B detect an abnormal condition of the process. In response to this, the mapping blocks 214A and 214B transmit alarm signals of process alarms to the operation monitoring terminal 2 via the message transmitter 13. Moreover, the function block 214-1C does not detect the abnormal condition of the process. Hence, the mapping block 215C does not transmit an alarm signal.

As described above, the system alarms during reset for the channel CH1 of the input/output module IOM2 and the channel CH2 of the input/output module IOM2, which are detected by the system diagnoser 211, are given due to the reset of the F & G devices 206-1 and 206-2, and are not appropriate alarms that should be originally detected. Therefore, the display of these system alarms should be suppressed.

However, there is no method for the system diagnoser 211 determining whether or not the system alarms have been given due to the reset of the F & G devices 206-1 and 206-2. Accordingly, it is difficult to suppress the display of the alarms. In order to make such a determination, it is required to input, into the system diagnoser 211, information that a reset signal from the reset switch has been inputted through which channel CH of which input/output interface, and accordingly which F & G device connected to which channel of which input/output module is during reset.

However, it is difficult in the control apparatus 1 of the safety instrumented system to make a mechanism that, when the safety instrumented system is being operated, can convey, to the system diagnoser 211, information that a reset signal from the reset switch of which channel CH of which input/output interface has been inputted, that is, mounting location information of the reset input (the reset switch). This is because the safety instrumented system is in conformity with the international standard IEC 61131-3.

In the configuration of FIG. 2, the reset signal from the reset switch 225 is inputted into the system diagnoser 211 via the input/output interface 220. However, as described above, it is difficult for the system diagnoser 211 to acquire the mounting location information of the reset switch 225 via the input/output interface 220. Hence, it is required to previously and manually make a definition by using an engineering terminal 3 to transmit the mounting location information of the reset switch 225 to the system diagnoser 211. However, this method increases engineering work load and also becomes a cause of a mistake, and accordingly is not realistic.

Moreover, the reset signal can also be inputted from instrument diagrams 2-1, 2-2, and 2-3 included in the operation monitoring terminal 2 into the function blocks 214-1A, 214-1B, and 214-1C via the mapping blocks 215A, 215B, and 215C. Furthermore, there is also a case where a reset signal transmitted from a tool (not illustrated) of another terminal via a network N resets the F & G device. It is conceivable that if the system diagnoser 211 can receive reset signals from these reset input devices, and further acquire the mounting locations of the reset F & G devices, the display of alarms can be suppressed. However, the safety instrumented system is in conformity with the international standard IEC 61131-3; accordingly, it is difficult for the system diagnoser 211 to acquire mounting location information of the F & G devices corresponding to the function blocks 214-1A, 214-1B, and 214-1C as in the case where it is difficult to acquire information of the mounting locations of the reset inputs. Hence, it is required to previously and manually make a definition by using the engineering terminal 3 to transmit the mounting location information of the F & G devices to the system diagnoser 211. However, this method is not realistic as in the case of the above reset switch 225.

In this manner, it is difficult for the system diagnoser 211 to acquire the mounting location into which a reset signal is to be inputted. Hence, it is difficult for the system diagnoser 211 to suppress the display of an alarm.

A reset signal is inputted into a reset input terminal of the function block irrespective of a portion of a reset input. Hence, the reset signal outputted from the function block 214-1A on the basis of the reset signal inputted into the function block 214-1A is connected to the system diagnoser 211. Accordingly, the system diagnoser 211 can determine whether or not the reset signal has been inputted. Hence, it is conceivable that if the system diagnoser 211 can acquire the mounting location of the reset F & G device, it is possible to suppress the display of an alarm.

The output signal of the F & G device 206-1 is transmitted to the function block via the system diagnoser 211. However, information on to which channel CH of which input/output interface the F & G device that has transmitted the output signal is connected is not conveyed to a terminal of the function block. Moreover, the function blocks 214-1A, 214-1B, and 214-1C are in conformity with the international standard IEC 61131-3. Accordingly, it is not realistic to make a mechanism to convey the information. Hence, even if a reset signal outputted from the function block is connected to the system diagnoser 211, it is difficult for the system diagnoser 211 to determine for which channel CH of which input/output interface the display of a system alarm is suppressed.

In terms of a process alarm, even if the application program does not detect or detects an abnormal condition of the process during reset of the F & G device, an annunciator message as an alarm of the process is not transmitted to the operation monitoring terminal 2. Accordingly, the sounding of a process alarm is suppressed.

Moreover, a reset signal is inputted into any function block. Accordingly, it is possible in the function block to determine whether or not a reset has been inputted. Hence, it is conceivable that if the function block further can acquire the mounting location information of all F & G devices reset concurrently, it makes it possible to suppress the display of an alarm. However, the function blocks 214-1A, 214-1B, and 214-1C are in conformity with the international standard IEC 61131-3. Accordingly, it is not realistic to make a mechanism to convey the information to the function block. Hence, it is difficult to suppress the display of a process alarm.

In this manner, in the configuration of the safety instrumented system illustrated in FIG. 2, it is difficult to appropriately suppress the display of a system alarm and/or a process alarm during reset of the F & G device. Hence, the display of a false alarm can confuse the operator.

One or more embodiments of the present invention provide a safety instrumented control apparatus and a method thereof, and a safety instrumented system that can appropriately suppress the display of an alarm for an F & G device during reset.

(1) A safety instrumented control apparatus according to one or more embodiments of the invention (the present safety instrumented control apparatus) includes: a message transmitter configured to transmit an alarm message to a display apparatus on the basis of an output from a field device that continues to output an alarm on the basis of detection of an abnormal condition until a reset operation is performed; a storage configured to store a group ID for identifying a group of the field devices; a reset manager configured to count on a timer until a predetermined amount of time passes after the reset operation; and a diagnoser configured to, during the count of the timer for any of the field devices belonging to the group ID, add display suppression information to the alarm message related to the field device belonging to the group ID.

(2) Moreover, in the present safety instrumented control apparatus, the storage may store definition information where information on channels connected to the field devices in input/output modules connected to the safety instrumented control apparatus is associated with the group IDs.

Furthermore, the diagnoser may refer to the definition information on the basis of the channel information of the input/output module that has received an output from the field device, and may identify the group ID to which the field device targeted for the reset operation belongs.

(3) Moreover, in the present safety instrumented control apparatus, the diagnoser may include a process alarm diagnose (process alarm diagnosing circuit).

The process alarm diagnoser may detect an abnormal condition in process control being a controlled target of the safety instrumented control apparatus on the basis of an output value of the field device, and may transmit a process alarm as the alarm message to be displayed on the display apparatus.

(4) Moreover, in the present safety instrumented control apparatus, the diagnoser may include a system diagnose (system diagnosing circuit).

The system diagnoser may diagnose at least any of the states of the safety instrumented control apparatus, the input/output module, and the field device, and their connection states on the basis of the output from the field device, may detect an abnormal condition of a system, and may transmit a system alarm as the alarm message to be displayed on the display apparatus.

(5) Moreover, in the present safety instrumented control apparatus, the display suppression information may be information that instructs the display apparatus to suppress the display of the alarm message, and to suppress the display of the alarm message may include not to display the alarm message or to display the alarm message in a form different from a normal form.

(6) Moreover, in the present safety instrumented control apparatus, the diagnoser may be configured to suppress the detection of an abnormal condition, or to suppress the transmission of the alarm message, during the count of the timer.

(7) Moreover, in the present safety instrumented control apparatus, the storage may store, as the definition information, information where reset identification information for identifying at least one or more field devices targeted for the reset operation is associated with the group ID.

The reset manager may refer to the definition information on the basis of the reset operation, identifies the group ID from the reset identification information, and may start counting on the timer for the group ID.

(8) Moreover, the present safety instrumented control apparatus may include a resetter configured to transmit a reset command to the input/output module.

The resetter may identify information on a channel connected to the field device on the basis of the reset operation, the definition information, and the reset identification information, and may transmit a reset command on the basis of the identified channel information.

Moreover, the safety instrumented control apparatus may include: a trip operation logic configured to shut down process control being a controlled target of the safety instrumented control apparatus upon having detected a trip on the basis of an output value of the field device; and an application program configured not to execute the trip operation logic upon the group ID to which the field device belongs being the same as the group ID to which a field device targeted for the reset operation, for which a timer is counting until a predetermined amount of time passes, even in a case where the trip has been detected on the basis of output values of at least one or more field devices.

(9) Moreover, the present safety instrumented control apparatus may further include: a record holder (record storage) where the alarm message is saved irrespective of whether or not during the count of the timer; and an activation state manager (activation state managing circuit) configured to manage an activation state of the field device.

Upon any of the field devices having not returned to a normal state after the end of the count of the timer, the diagnoser may retransmit, to the display apparatus, the alarm message during the count of the timer saved in the record holder.

(10) A safety instrumented system according to one or more embodiments of the invention (the present safety instrumented system) may include: the present safety instrumented control apparatus; and an engineering terminal configured to previously define group IDs for identifying groups including the field devices predetermined as targets for suppressing the display of an alarm on the display apparatus and/or definition information where information on channels connected to the field devices in input/output modules connected to the safety instrumented control apparatus is associated with the group IDs, and download the group IDs and/or the definition information to the storage of the safety instrumented control apparatus.

(11) Moreover, the present safety instrumented system may further include a display apparatus configured to receive an alarm message transmitted from the safety instrumented control apparatus via a network, suppress the display of the alarm message upon display suppression information having been added to the alarm message, and display the alarm message upon the display suppression information having not been added to the alarm message.

(12) A plant control method according to one or more embodiments of the invention (the present plant control method) includes: transmitting an alarm message to a display apparatus on the basis of an output from a field device that continues to output an alarm on the basis of detection of an abnormal condition until a reset operation is performed; storing a group ID for identifying a group of the field devices; counting on a timer until a predetermined amount of time passes after the reset operation; and during the count of the timer for any of the field devices belonging to the group ID, adding display suppression information to the alarm message related to the field device belonging to the group ID.

(13) Moreover, the present plant control method may further include: storing definition information where information on channels connected to the field devices in input/output modules is associated with the group IDs; and referring to the definition information on the basis of the channel information of the input/output module that has received an output from the field device, and identifying the group ID to which a field device targeted for the reset operation belongs.

According to one or more embodiments of the invention, it is possible to suppress an alarm generated by resetting a power supply of the field device (the F & G device) from being displayed on the display apparatus (the operation monitoring terminal). Therefore, it is possible to reduce the confusion of an operator based on the display of a false alarm.

As a specific example of the safety instrumented system, an FGS (fire and Gas System) is described. The FGS is a system constructed for suppressing the spread of an event that has occurred in a structure such as a building or a plant. Examples of F & G devices used to construct the FGS include, for example, a gas detector, a flame detector, a heat detector, and a smoke detector. If an abnormal condition occurs in, for example, a plant (for example, if abnormally much smoke, flame, or the like is generated), a measurement value of the F & G device is, for example, a value exceeding a predetermined threshold. The F & G device outputs an alarm or an alarm value when the measurement value exceeds the predetermined threshold. Once the measurement value has exceeded the threshold, the F & G device continues to output the alarm or alarm value even after the measurement value falls to less than the threshold. This is because an abnormal condition that has occurred in a plant or the like is surely notified. It has been mentioned that if an abnormal condition occurs, the measurement value of the F & G device exceeds the predetermined threshold. The F & G device, however, may not be configured in this manner.

FIG. 1 is a configuration diagram illustrating a safety instrumented system according to one or more embodiments of the invention. As illustrated in FIG. 1, a safety instrumented system 100 mainly includes a safety control apparatus (hereinafter referred to as the control apparatus) 1 such as a safety controller, an operation monitoring terminal 2, an engineering terminal 3, input/output interfaces 4-1 and 4-2, and F & G devices 6-1 to 6-3. The control apparatus 1 includes a system diagnoser (diagnoser) 11, a reset manager 12, a message transmitter 13, an application executor 14, a DCS integrator 15, a storage 16, a resetter 17, and a database 18, all of which may be implemented by hardware (e.g., circuit), software, or a combination thereof. The input/output interface 4-1 includes a power supply (PS) 7-1. The input/output interface 4-2 includes a power supply (PS) 7-2.

In the example illustrated in FIG. 1, one control apparatus 1 includes two input/output interfaces 4-1 and 4-2. This configuration is an example. One control apparatus 1 can also include one, or three or more input/output interfaces. Moreover, in the example illustrated in FIG. 1, one input/output interface 4-1 includes one power supply (PS) 7-1, and is connected to two F & G devices 6-1 and 6-2. Furthermore, one input/output interface 4-2 includes one power supply (PS) 7-2, and is connected to one F & G device 6-3. These configurations are examples. The input/output interfaces 4-1 and 4-2 can also be connected to three or more F & G devices, and include three or more power supplies.

The control apparatus 1, the operation monitoring terminal 2, and the engineering terminal 3 are connected via, for example, a network N such as Ethernet (registered trademark). The operation monitoring terminal 2 is operated by, for example, an operator of a plant. The operation monitoring terminal 2 is an apparatus used for monitoring the process, as an integrated environment of a process control system and the safety instrumented system 100. The engineering terminal 3 is an apparatus for creating a program to be executed by the control apparatus 1. Moreover, the engineering terminal 3 is also used to create data used to execute a program, and to make various settings of the control apparatus 1, in addition to the creation of the program. The operation monitoring terminal 2 and the engineering terminal 3 may be realized by one terminal.

The control apparatus 1 is an apparatus used to download an application created by the engineering terminal 3 from the engineering terminal 3, and execute plant shutdown and other logic. The control apparatus 1 includes the application executor 14 and the storage 16. A program (application logic) to be executed by the application executor 14 is stored in the storage 16. The application logic is set by the engineering terminal 3, and downloaded to the control apparatus 1. The application logic is described in, for example, a functional block diagram (FBD: Functional Block Diagram) format by using a graphical user interface such as the engineering terminal 3. The function block is a unit having functions such as computation and control, which operates in a controller to control a field device. Various types such as a general computation process, an input instruction, a manual operation, a signal selection, and a signal setting related to an analog signal or contact signal are prepared as the functions of the function block. The control apparatus 1 downloads the application logic created by the engineering terminal 3 as the program to the storage 16, and stores the application logic therein.

As illustrated in FIG. 1, the F & G devices 6-1 to 6-3 are connected to the control apparatus 1 via wiring and the input/output interfaces. The control apparatus 1 receives alarms or alarm values outputted from the F & G devices 6-1 to 6-3. Function blocks 14-1A, 14-1B, and 14-1C in the application executor 14 of the control apparatus 1 detect the alarms or alarm values. Mapping blocks 15A, 15B, and 15C of the DCS integrator 15 transmit alarm signals indicating that the F & G devices 6-1 to 6-3 have detected abnormal conditions to the operation monitoring terminal 2 via the message transmitter 13.

Here, the mapping blocks 15A, 15B, and 15C are application logic for converting data to be used in the safety instrumented system into a format that can be directly handled by the operation monitoring terminal 2 being a DCS integrated environment. The mapping blocks 15A, 15B, and 15C are created associated with the function blocks (the application logic to be executed by the application executor 14). In other words, the mapping block 15A and the function block 14-1A, the mapping block 15B and the function block 14-1B, and the mapping block 15C and the function block 14-1C are paired, respectively. Moreover, the mapping blocks 15A, 15B, and 15C convert the alarms detected by the function blocks 14-1A, 14-1B, and 14-1C into a format that can be displayed on the operation monitoring terminal 2.

The message transmitter 13 transmits, to the operation monitoring terminal 2, alarm signals for the abnormal conditions detected by the system diagnoser 11, and the mapping blocks 15A, 15B, and 15C. The operation monitoring terminal 2 receives the alarm signals. If the received alarm signals are related to abnormal conditions of the process, the contents of the alarms are displayed on a process alarm view 22. If the received alarm signals are related to abnormal conditions of the system, the contents of the alarms are displayed on a system alarm view 23. Alarm messages are displayed sequentially from the latest in list form on the process alarm view 22 and the system alarm view 23. The operator of the plant checks the contents of the displayed alarm messages.

The system diagnoser 11 diagnoses abnormal conditions of the safety instrumented system 100. The system diagnoser 11 compares measurement values received by the control apparatus 1 from the F & G devices 6-1 to 6-3 with predetermined thresholds. If an abnormal condition such as a break has been detected, the control apparatus 1 transmits an alarm signal to the operation monitoring terminal 2 via the message transmitter 13. The operation monitoring terminal 2 displays the received alarm signal as a system alarm on the system alarm view 23.

The operation monitoring terminal 2 includes an unillustrated display, input, and communication device. The display is a display apparatus such as a liquid crystal display. The input includes input devices such as a keyboard and a mouse. The communication device communicates with the control apparatus 1 via the network N.

As described above, the F & G devices 6-1 to 6-3 continue to output alarms or alarm values even after causes of abnormal conditions are solved. In order to clear the alarms of the F & G devices 6-1 to 6-3, resets are performed by turning off the power to the F & G devices 6-1 to 6-3 and then turning on the power. Operation methods for resetting the F & G device includes a method including two operations in all, a turning-on operation and a turning-off operation, and a method in which turning on and turning off are performed in one operation. The decision on which method is used depends on the application to be constructed.

When the communication device of the operation monitoring terminal 2 has received an alarm signal from the control apparatus 1, the content (including at least an alarm value) of the alarm is displayed on the display. Consequently, the operator of the plant can grasp the place where in the plant the abnormal condition has occurred and/or the content of the abnormal condition. Therefore, the operator can take a measure to solve the abnormal condition.

The content of the alarm is displayed on window screens of software such as the process alarm view 22, the system alarm view 23, and the instrument diagrams 2-1 to 2-3. Moreover, the control apparatus 1 designates an alarm level (for example, a critical alarm, a major alarm, a minor alarm, a recording alarm, or a reference alarm) of the alarm signal. The content of the alarm, together with the alarm level, is displayed. Moreover, the control apparatus 1 can also be set in such a manner as not to display the content of the alarm by designating hide, depending on the alarm signal.

The operator of the plant confirms the solution of the abnormal condition being the cause of the alarm, and then performs an operation for resetting the F & G device if necessary. It is assumed, for example, that an alarm status indicating the occurrence of a process alarm of the F & G device 6-1 is being displayed on the instrument diagram 2-1. In this case, the function block 14-1A is in a state of continuing to detect the alarm, or the F & G device is in a state of continuing to output the alarm value. Hence, in order to clear the state and return to a normal operating state, the operator performs a reset operation by using a reset input of the instrument diagram 2-1. The reset operation is transmitted from the instrument diagram 2-1 to the function block 14-1A via the mapping block 15A. As a result, the reset signal is inputted into the reset manager 12 and the resetter 17 via a reset variable 19-1.

The instrument diagram is a window screen constructed by software for operating and monitoring field devices (including the F & G devices) being control targets of the process control system and/or the safety instrumented system.

The instrument diagrams 2-1 to 2-3 each include a reset input. Moreover, the instrument diagrams 2-1 to 2-3 are connected respectively to the mapping blocks 15A, 15B, and 15C of the DCS integrator 15 of the control apparatus 1 via the network N. The mapping block 15A and the function block 14-1A, the mapping block 15B and the function block 14-1B, and the mapping block 15C and the function block 14-1C are paired, respectively, and are connected to each other. The function blocks 14-1A, 14-1B, and 14-1C output reset signals. The function blocks 14-1A, 14-1B, and 14-1C are connected to the reset manager 12 and the resetter 17 via the reset variables 19-1 to 19-3. The reset variable may be an example of reset identification information.

The reset variables 19-1 to 19-3 are variables handled to transmit the reset signals for the F & G devices 6-1 to 6-3 to the reset manager 12 and the resetter 17. The reset variables 19-1 to 19-3 convert the reset signals, and input/output interface (input/output module) identification numbers (for example, IOM: IOM1, IOM2), channel identification numbers (for example, CH: CH1, CH2), and reset group IDs (for example, ID: 1, 2), which are assigned to the input/output interfaces (the input/output modules) 4-1 and 4-2, into information (signals) that can be handled. Variable names of the reset variables 19-1 to 19-3 are used for definition in a table 20 described below. As illustrated in FIG. 1, names I1-C1, I1-C2, and I2-C1 are assigned to the reset variables 19-1, 19-2, and 19-3, respectively.

Moreover, the relationship between these reset variables 19-1, 19-2, and 19-3, and the identification numbers (for example, IOM: IOM1, IOM2) of the input/output modules electrically connected to the control apparatus 1, their channels (for example, CH: CH1, CH2), and predetermined reset group IDs (for example, ID: 1, 2) is stored in the table 20 of the database (storage) 18.

Here, the reset group indicates a group of F & G devices that are reset concurrently when one reset input resets the F & G devices. A reset group ID is an identification number of the reset group. A user sets a reset group ID by using the engineering terminal 3. A description is given below of how the reset manager 12 and the resetter 17 use the reset variables 19-1 to 19-3 and the table 20.

For example, definition information (for example, the table 20) where information on a channel to which the F & G device (field device) is connected in the input/output module connected to the control apparatus 1 is associated with a group ID is stored in the database (storage) 18.

The F & G devices 6-1 and 6-2 are connected to the power supply (PS) 7-1 built in the input/output interface 4-1. Moreover, the F & G device 6-3 is connected to the power supply (PS) 7-2 built in the input/output interface 4-2.

The relationship between the input/output interfaces (input/output modules) 4-1 and 4-2 on which the F & G devices 6-1, 6-2, and 6-3 are mounted, and their channels, the names of the reset variables, and the reset group IDs is previously defined by the engineering terminal 3, and is saved as the table 20 in the database 18 of the control apparatus.

The resetter 17 transmits reset commands in formats appropriate for the input/output interfaces 4-1 and 4-2 on the basis of the reset signals outputted from the function blocks 14-1A, 14-1B, and 14-1C via the reset variables 19-1, 19-2, and 19-3. The resetter 17 checks whether or not it is necessary to transmit a reset command for all the input/output modules (IOM) and channels (CH) in every scan being an operating cycle of the control apparatus 1. In other words, the resetter 17 refers to the names of the reset variables 19-1 to 19-3 set for the channels (CH) on the basis of the above-mentioned table 20 to make the above check. The resetter 17 transmits a reset command to an IOM and a CH, which are processing targets, on the basis of a check result.

When the reset signal is outputted via the reset variable 19-1, a transmission destination of a reset command is the input/output interface 4-1 having the identification number of IOM1. The input/output interface 4-1, which has received the reset command, temporarily turns off the built-in power supply (PS) 7-1. Consequently, the power supplied from the power supply (PS) 7-1 to the F & G devices 6-1 and 6-2 is temporarily shut off. Accordingly, the F & G devices 6-1 and 6-2 are reset. The input/output interface 4-2, which has received the reset command, also temporarily turns off the build-in power supply (PS) 7-2 likewise. Consequently, the power supplied from the power supply (PS) 7-2 to the F & G device 6-3 is temporarily shut off. Accordingly, the F & G device 6-3 is reset.

There are several types of input/output interfaces. A reset method may be different depending on the type.

A first method is employed when the input/output interfaces 4-1 and 4-2 have a function of resetting the power supplies (PS) 7-1 and 7-2. In this method, the resetter 17 transmits an instruction to reset the power supplies (PS) 7-1 and 7-2 as the reset command to the input/output interfaces 4-1 and 4-2.

A second method is employed when the input/output interfaces 4-1 and 4-2 include power supplies (not illustrated) respectively for their channels CH, and when the input/output interfaces 4-1 and 4-2 have a function of resetting the power supply for each CH. In this method, the resetter 17 transmits an instruction to designate CH of the input/output interface 4-1 or 4-2 connected to a reset target F & G device and reset a relevant power supply, as the reset command, to the input/output interface 4-1 or 4-2.

In this manner, the resetter 17 includes some known reset methods, and transmits an appropriate reset command according to the type of input/output interface.

The power supplies (PS) 7-1 and 7-2 for supplying the power to the F & G devices 6-1 to 6-3 are built in the input/output interfaces 4-1 and 4-2. Instead of this, each of the power supplies (PS) 7-1 and 7-2 may be realized by a combination of an external power supply and a relay circuit.

Moreover, other than the above configuration, the reset input may be realized by a software tool included in a terminal other than the operation monitoring terminal 2.

The reset manager 12 has a function of grasping whether or not the F & G devices 6-1 to 6-3 are during reset according to the reset group IDs. The reset manager 12 is connected to reset signals from the function blocks 14-1A, 14-1B, and 14-1C. The reset manager 12 includes a timer (not illustrated) for each reset group ID. The reset manager 12 refers to the table 20 to be referred to in the database 18, and identifies a reset group ID in accordance with the reset signal on the basis of the name of the reset variable. Furthermore, the reset manager 12 starts the timer for the identified reset group ID. The started timer finishes the count after the elapse of a fixed amount of time (timer count time). During the count of the timer indicates that the F & G device of the reset group ID is during reset. The timer count time is preset by the user via the engineering terminal 3. The reset manager 12 may use an address of the reset variable to check the name of the reset variable against the table 20.

The reset manager 12 handles a reset flag and a timer value as illustrated in a table in a bottom right portion of FIG. 1. Specifically, the reset manager 12 includes a table 21 illustrating the relationship between a reset group ID (ID), a reset flag, and a timer value, and updates the table 21 on the basis of the operation of the timer.

When having received a reset signal from the function block 14-1A via the reset variable 19-1, the reset manager 12 checks the name I1-C1 of the reset variable 19-1 against the table 20 referred to in the database 18. The reset manager 12 identifies the reset group ID as 1 when the reset signal is inputted into the reset variable I1-C1.

The reset manager 12 starts the timer (not illustrated) provided in the reset manager 12, the timer corresponding to the value 1 of the reset group ID. In this case, as illustrated in the table 21 of FIG. 1, the value of a reset flag corresponding to the value 1 of the reset group ID becomes TRUE. The timer value is updated to a timer count value 2000 ms being the remaining time before the end of the count. In the table 21 of the reset manager 12, when the timer (not illustrated) finishes the count after a predetermined period, the timer value is updated to 0, and the reset flag (reset flag value) to FALSE. The predetermined period during which the timer (not illustrated) counts is a value preset by using the engineering terminal 3.

The reset manager 12 handles the F & G device as during reset while the reset flag is TRUE. Here, during reset indicates a reset state, that is, a state where a reset has not yet been completed. The reason that the timer counts the predetermined period is because it takes the F & G devices 6-1 to 6-3 a fixed amount of time to start a reset, be reactivated, and enter the operating state.

A description is given of a method for suppressing the display of a system alarm as a first method for suppressing the display of an alarm. The system diagnoser 11 refers to the table 20 of the database 18 when having detected an abnormal condition of the system. The system diagnoser 11 can acquire information on the input/output module identification number (IOM) and the channel identification number (CH), which indicate the mounting location of the F & G device where the abnormal condition of the system has been detected. Hence, the system diagnoser 11 can identify a reset group ID by referring to the table 20. For example, as illustrated in the table 20 of FIG. 1, when, in the signal, the input/output module identification information (IOM) is 1, and the channel identification number (CH) is 1, the reset group ID is 1. The system diagnoser 11 refers to a reset flag of the identified reset group ID in the reset manager 12 (the table 21).

When the reset flag of the reset group ID to which the F & G device where the abnormal condition of the system has been detected belongs is TRUE, the system diagnoser 11 transmits an alarm signal that has designated "hide" as display suppression information to the operation monitoring terminal via the message transmitter 13. The operation monitoring terminal 2 receives the alarm signal via the communication device (not illustrated). "Hide" has been designated as the display suppression information in the alarm signal. Accordingly, a controller (not illustrated) of the operation monitoring terminal 2 does not display the content of the alarm under control over the display (not illustrated).

The reset operation is then performed on the F & G device 6-1. When an abnormal condition of the system related to CH1 of the input/output interface 4-1 has been subsequently detected, the system diagnoser 11 transmits an alarm signal that has designated "hide", to the operation monitoring terminal via the message transmitter 13 after confirming that the reset flag of the value 1 of the reset group ID is TRUE in the reset manager 12 (the table 21). Consequently, it is possible to appropriately suppress an alarm during reset of the F & G device 6-1, that is, an alarm generated due to the reset state of the F & G device 6-1 from being displayed on the operation monitoring terminal 2.

A description is given of a method for suppressing the display of a process alarm as a second method for suppressing the display of an alarm. When having detected an abnormal condition of the process on the basis of an output value of the F & G device 6-1, the function block 14-1A refers to a reset group ID 14-3A set for the function block 14-1A. The reset group IDs 14-3A, 14-3B, and 14-3C, which are set respectively for the function blocks 14-1A to 14-1C, are preset by using the engineering terminal 3. The function block 14-1A refers to a reset flag of the reset group ID 14-3A set for the function block 14-1A in the reset manager 12 (the table 21).

The function blocks 14-1A to 14-1C may be process alarm diagnosers. In other words, the function blocks 14-1A to 14-1C may be configured in such a manner as to detect an abnormal condition in process control being a controlled target of the control apparatus 1 on the basis of an output value of the F & G device, and transmit a process alarm as an alarm message to be displayed on the operation monitoring terminal 2.

When the reset flag of the reset group ID to which the F & G device where the abnormal condition of the process has been detected belongs is TRUE, the function block 14-1A transmits an alarm signal that has designated "hide" from the mapping block 15A to the operation monitoring terminal 2 via the message transmitter 13. The operation monitoring terminal 2 receives the alarm signal via the communication device (not illustrated). "Hide" has been designated for the alarm signal. Accordingly, the controller (not illustrated) of the operation monitoring terminal 2 does not display the content of the alarm under control over the display (not illustrated).

Due to the performance of the reset operation on the F & G device 6-1, the function block 14-1A may detect an abnormal condition of the process, which is a break in the F & G device 6-1 connected to CH1 of the input/output interface 4-1. In this case, when having confirmed that the reset flag of the value 1 of the reset group ID is TRUE in the reset manager 12 (the table 21), the function block 14-1A transmits an alarm signal that has designated "hide" from the mapping block 15A to the operation monitoring terminal via the message transmitter 13. Consequently, it is possible to appropriately suppress an alarm during reset of the F & G device 6-1, that is, an alarm generated due to the reset state of the F & G device 6-1 from being displayed on the operation monitoring terminal 2. The case where an abnormal condition of the process, which is a break in the F & G device 6-1, has been detected may include a case where an abnormal condition of the process has been detected from a measurement value of the F & G device 6-1. Moreover, the function blocks 14-1B and 14-1C also operate as in the function block 14-1A. Furthermore, the mapping blocks 15B and 15C also operate as in the mapping block 15A.

A third method for suppressing the display of an alarm is described. As described above, the system diagnoser 11 and the mapping blocks 15A, 15B, and 15C transmit an alarm signal that has designated "hide" via the message transmitter 13 to suppress the display of an alarm. In addition to such a method for suppressing the display of an alarm, the system diagnoser 11 and the mapping blocks 15A, 15B, and 15C may be configured to designate an alarm level lower than normal for an alarm signal and transmit the alarm signal. In this case, the content of the alarm, together with the alarm level lower than normal, is displayed on the display of the operation monitoring terminal 2. An alarm message is displayed in a form different from a normal form. Accordingly, the confusion of the operator of the plant caused by a false alarm generated by the reset state of the F & G device is reduced.

A fourth method for suppressing the display of an alarm is described. The system diagnoser 11 and/or the mapping blocks 15A, 15B, and 15C may be configured in such a manner as not to transmit an alarm signal while the reset flag is TRUE. In this case, the content of an alarm is not displayed on the display of the operation monitoring terminal 2. Hence, the confusion of the operator of the plant caused by a false alarm is reduced. Not to transmit an alarm signal may include to stop alarm detection itself.

If a true abnormal condition (such as a break) occurs during reset of the F & G device, the display of the true alarm on the operation monitoring terminal 2 is also suppressed. However, it is essentially preferable that the true alarm be displayed on the operation monitoring terminal 2 as usual. Hence, if the display of the true alarm is suppressed, a measure described below is taken to display the true alarm after the end of the timer count.

The control apparatus 1 includes a record holder and an activation state manager. For example, the storage 16 can function as the record holder. Furthermore, the reset manager 12 can function as the activation state manager. A message of a system alarm and a message of a process alarm are saved in the record holder irrespective of whether or not during reset. The activation state manager manages whether or not all the F & G devices being monitoring targets have returned to normal after the reset. The system diagnoser 11 checks the activation state manager after the end of the timer count and, if any of the field devices has not returned, retransmits an alarm message of the system during reset saved in the record holder to the operation monitoring terminal 2 without designating "hide". The mapping blocks 15A, 15B, and 15C diagnose (confirm) the occurrence of a process alarm after the end of the timer count. When having detected, for example, a break as an abnormal condition of the process, the mapping blocks 15A, 15B, and 15C retransmit an alarm message of the process during reset saved in the record holder to the operation monitoring terminal 2 without designating "hide". The message of the process alarm saved in the record holder may include only a message indicating a break.

In the safety instrumented system of one or more embodiments, the function blocks 14-1A, 14-1B, and 14-1C of the application executor 14 include trip operation logics 14-2A, 14-2B, and 14-2C, respectively. The trip operation logics 14-2A, 14-2B, and 14-2C are a function of shutting down the plant to stop the operation of the plant safely when having detected a trip. When having detected a trip, the function blocks 14-1A, 14-1B, and 14-1C refer to the reset manager 12 (the table 21) and, if the reset flags of the reset group IDs 14-3A, 14-3B, and 14-3C set for the function blocks are TRUE, do not activate the trip operation logics connected to the function blocks. Consequently, it is possible to suppress a shutdown of the plant due to the detection of a false trip based on reset of the F & G device. Therefore, it is possible to suppress the occurrence of a loss in the plant due to an unnecessary shutdown of the plant caused by a false trip.

Output destinations, in the operation monitoring terminal 2, of alarms of the process control system and/or the safety instrumented system include the system alarm view 23, the process alarm view 22, the instrument diagrams 2-1 to 2-3, an integrated alarm management function (not illustrated), and a historical function (not illustrated) that collects alarm messages. In one or more embodiments, the display of alarms during reset of the F & G device on the system alarm view 23 and the process alarm view 22 is suppressed.

In terms of the display on the system alarm view 23 and the process alarm view 22, a message to the effect that it is during reset is not displayed concurrently with the display of an alarm, and only an alarm signal is displayed unlike the instrument diagrams 2-1 to 2-3. Accordingly, it is necessary to suppress the display of an alarm triggered by a reset.

As described above, the resetter 17 of one or more embodiments corresponds to some known input/output interfaces. Hence, for example, even if an input/output interface including a power supply per channel CH becomes widespread in the future and this input/output interface replaces the existing input/output interface, it is possible to continue to use the resetter 17 without changing the design.

Figure 3:
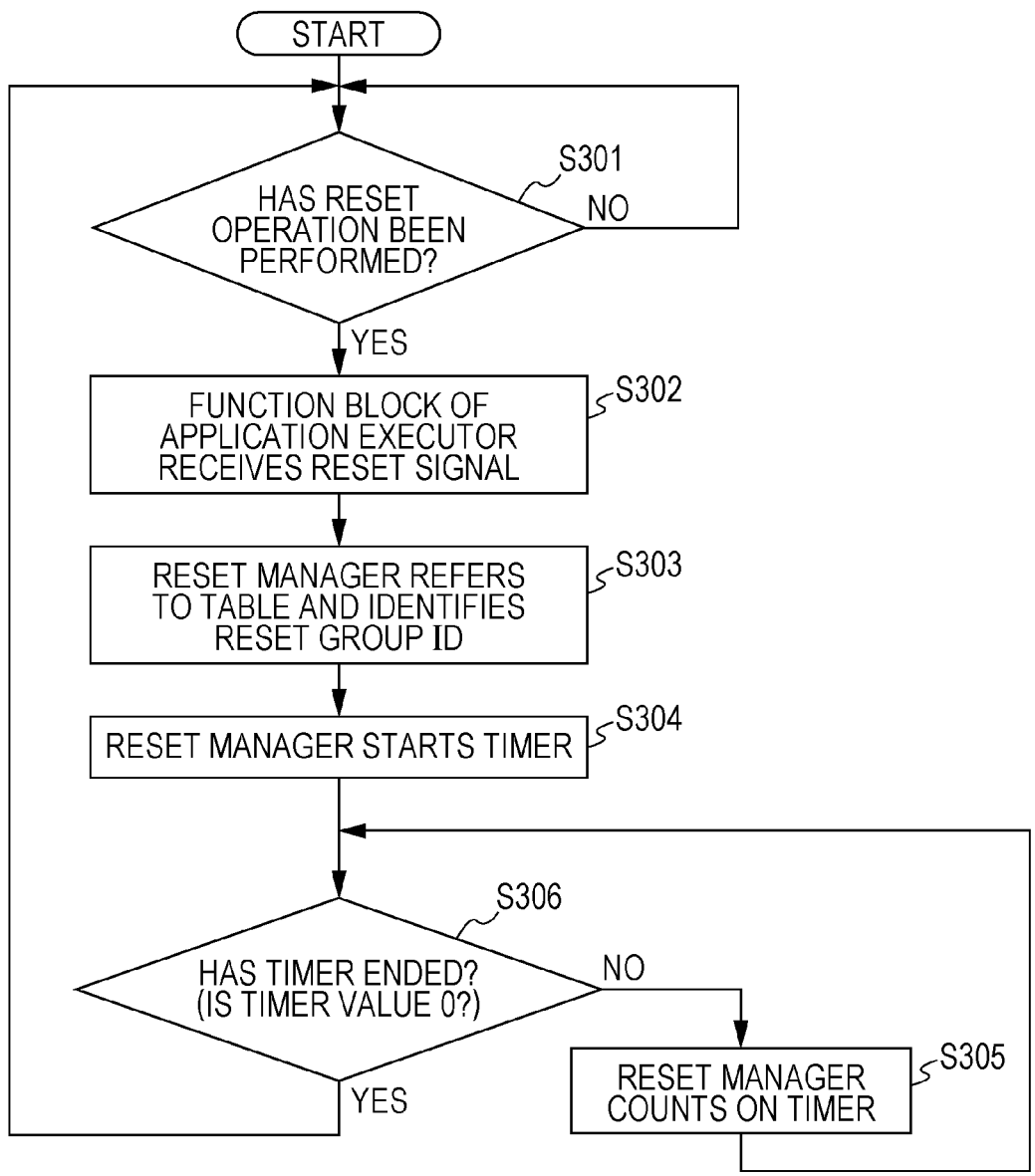
FIG. 3 is a flowchart of a reset manager according to one or more embodiments of the invention.

FIG. 3 is a flowchart describing the operation of the reset manager 12 of the safety instrumented system 100 of one or more embodiments.

In step S301, it is checked whether or not a reset operation has been inputted in the instrument diagrams 2-1 to 2-3 including the reset inputs. When a reset input operation has been performed via the reset input of any of the instrument diagrams 2-1 to 2-3 in step S301, the reset manager 12 of the control apparatus 1 determine that the reset operation has been inputted, and proceeds to step S302.

In step S302, the function block 14-1A, 14-1B, or 14-1C of the application executor 14 receives a reset signal from the reset input of any of the instrument diagrams 2-1 to 2-3. In step S303, the reset manager 12 refers to the table 20, and identifies a reset group ID on the basis of the name of a reset variable. An address of the reset variable may be used instead of the name of the reset variable.

In step S304, the reset manager 12 controls the built-in timer and causes the timer corresponding to the identified reset group ID to start counting. In step S306, the reset manager 12 determines whether or not the count of the timer has ended on the basis of a preset count value. When having determined in step S306 that the count of the timer has ended, the reset manager 12 returns to step S301. In other words, the reset manager 12 enters a state of waiting for the reset operation from the reset input of any of the instrument diagrams 2-1 to 2-3.

Moreover, when having determined in step S306 that the count of the timer has not ended, the reset manger 12 moves to step S305. In step S305, the resetter 17 controls the built-in timer to continue counting. That the count of the timer in the reset manager 12 has not ended indicates that the F & G device is during reset.

Figure 4:
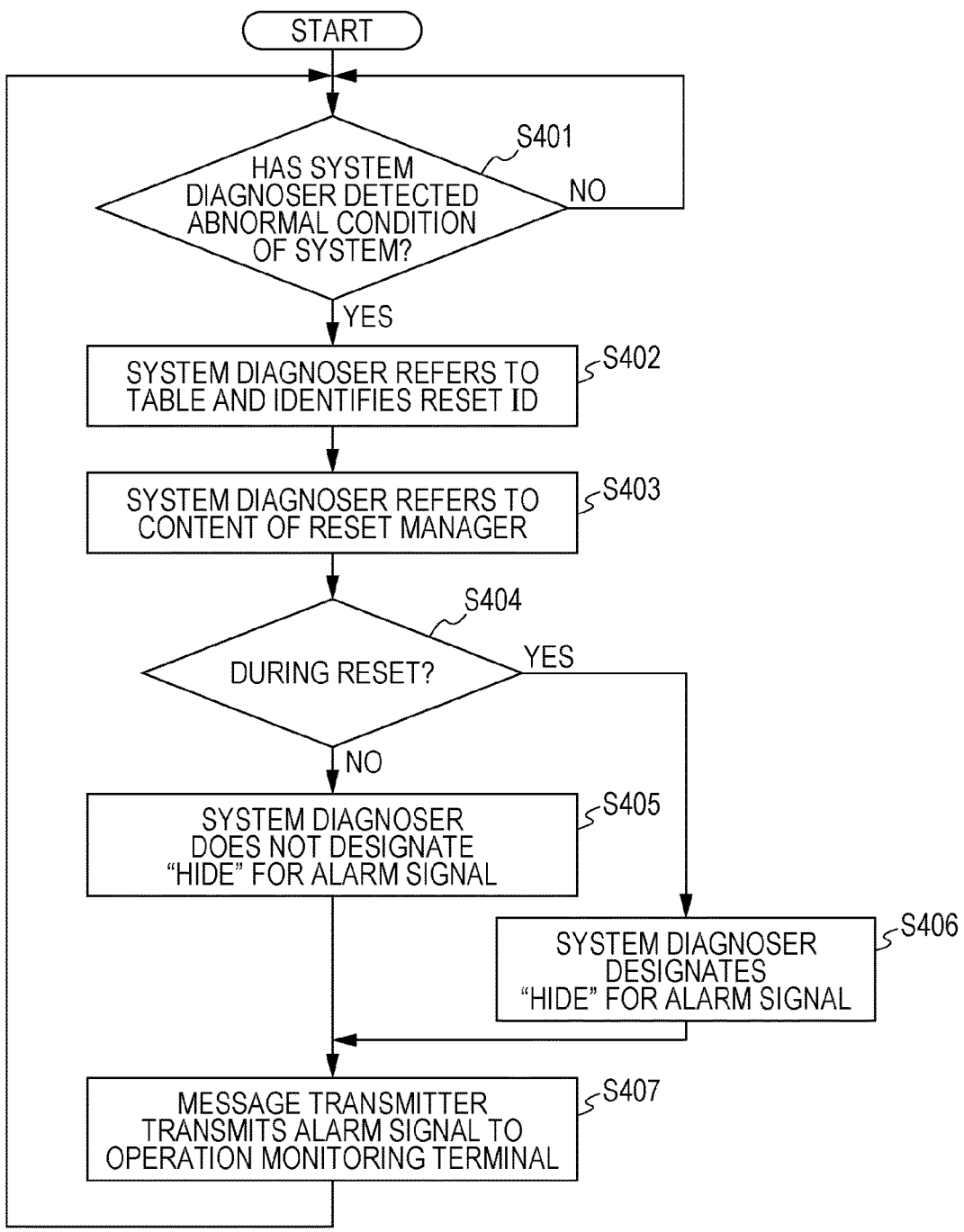
FIG. 4 is a flowchart of the issuance of a system alarm according to one or more embodiments of the invention.

FIG. 4 is a flowchart describing an operation of issuing a system alarm of the safety instrumented system 100 according to one or more embodiments.

In step S401, the system diagnoser 11 checks whether or not an abnormal condition (for example, a break) of the system has occurred. When having detected an abnormal condition of the system in step S401, the system diagnoser 11 proceeds to step S402.

In step S402, the system diagnoser 11 refers to the table 20 of the database 18, and identifies a group ID of a reset group from an input/output module identification number (IOM) and a channel identification number (CH), which indicate the mounting location of the F & G device where the abnormal condition of the system has been detected.

In step S403, the system diagnoser 11 refers to a reset flag or timer value of the identified reset group ID, which is the content of the reset manager 12 (the table 21), and proceeds to step S404.

In step S404, the system diagnoser 11 determines whether or not the device belonging to the identified reset group is during reset, on the basis of the referred reset flag value or timer value. If the reset flag value referred to in step S403 is TRUE, or if the timer value is during the count, the system diagnoser 11 determines that the above device is during reset, and proceeds to step S406.

In step S406, the system diagnoser 11 designates "hide" for an alarm signal, and proceeds to step S407. In step S407, the message transmitter 13 transmits the alarm signal where that has designated "hide" to the operation monitoring terminal 2. If the reset flag value referred to in step S403 is FALSE, or if the timer value is 0, the system diagnoser 11 determines that the above device is not during reset, and proceeds to step S405. In step S405, the system diagnoser 11 does not designate "hide" for an alarm signal and proceeds to step S407. In step S407, the message transmitter 13 transmits the alarm signal that has not designated "hide" to the operation monitoring terminal 2.

Figure 5:
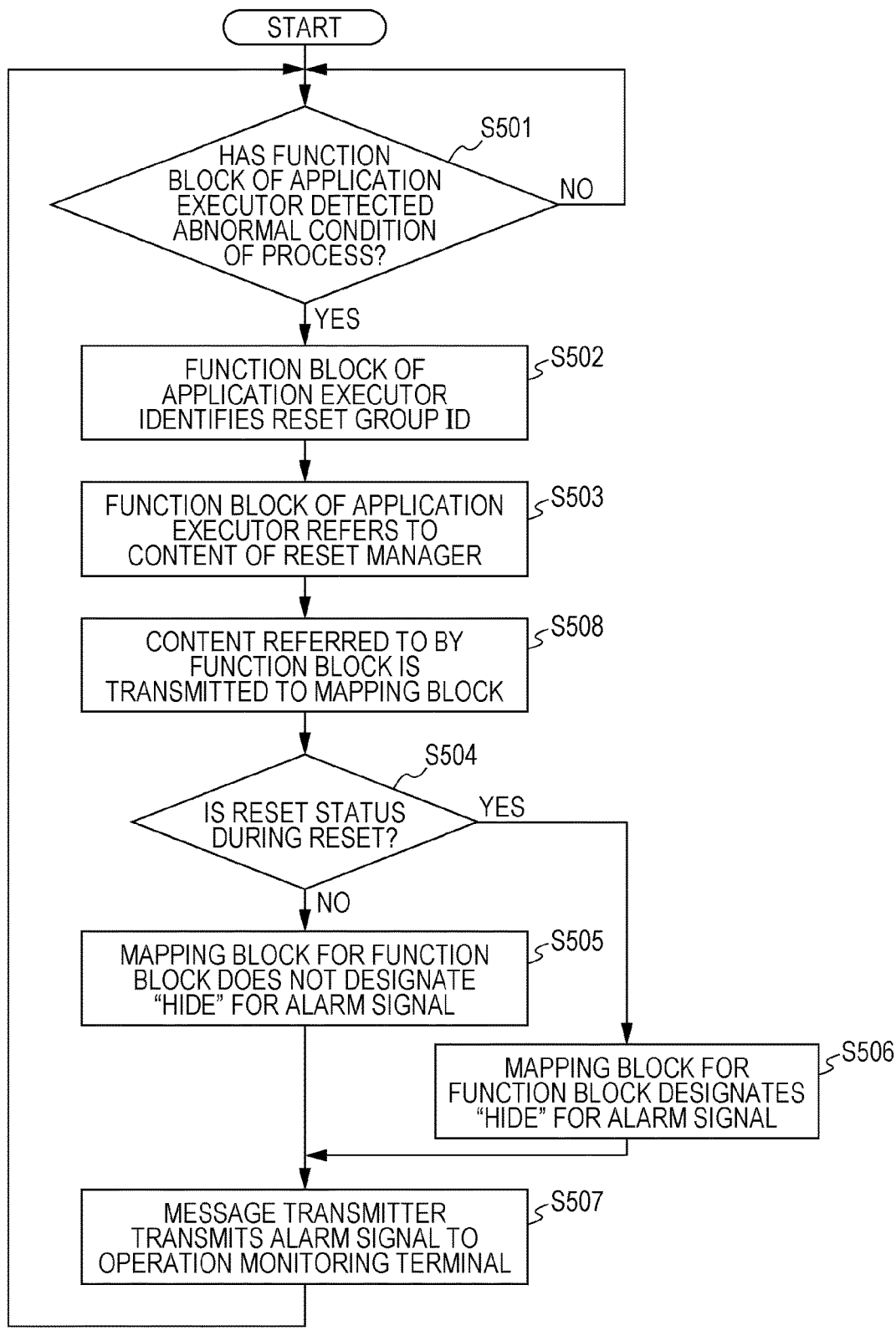
FIG. 5 is a flowchart of the issuance of a process alarm according to one or more embodiments of the invention.

FIG. 5 is a flowchart describing an operation of issuing a process alarm of the safety instrumented system 100 according to one or more embodiments.

In step S501, the function blocks 14-1A, 14-1B, and 14-1C of the application executor 14 check whether or not an abnormal condition of the process has occurred. When any of the function blocks 14-1A, 14-1B, and 14-1C of the application executor 14 has detected an abnormal condition of the process in step S501, it proceeds to step S502.

In step S502, the function block 14-1A, 14-1B, or 14-1C, which has detected the abnormal condition of the process, refers to the reset group ID 14-3A, 14-3B, or 14-3C preset for itself in the engineering terminal 3, and identifies a reset group ID to which the F & G device where the abnormal condition of the process has occurred belongs.

In step S503, the function block 14-1A, 14-1B, or 14-1C of the application executor 14 refers to the content of the reset manger 12, that is, a reset flag or timer value of the identified reset group ID, and proceeds to step S508.

In step S508, information on whether or not the device belonging to the identified reset group ID referred to by the function block 14-1A, 14-1B, or 14-1C of the application executor 14 is during reset is transmitted to the mapping block 15A, 15B, or 15C. Execution proceeds to step S504. The information on whether or not the above device is during reset may be a reset flag value or a timer value.

In step S504, the mapping block 15A, 15B, or 15C of the DCS integrator 15 determines whether or not the above device is during reset on the basis of the reset flag value or timer value referred to by the function block 14-1A, 14-1B, or 14-1C. If the information on whether or not the above devices is during reset, which was referred to in step S503, indicates during reset, the mapping block 15A, 15B, or 15C of the DCS integrator 15 determines that the above device is during reset, and proceeds to step S506.

In step S506, the mapping block 15A, 15B, or 15C of the DCS integrator 15 designates "hide" for an alarm signal corresponding to the detected alarm, and proceeds to step S507. In step S507, the message transmitter 13 transmits the alarm signal that has designated "hide" to the operation monitoring terminal 2. If the reset flag value referred to in step S503 is FALSE, or if the timer value is 0, the mapping block 15A, 15B, or 15C of the DCS integrator 15 determines that the above device is not during reset, and proceeds to step S505.

In step S505, the mapping block 15A, 15B, or 15C of the DCS integrator 15 does not designate "hide" for the alarm signal corresponding to the detected alarm, and proceeds to step S507. In step S507, the message transmitter 13 transmits the alarm signal that has not designated "hide" to the operation monitoring terminal 2.

Figure 6:
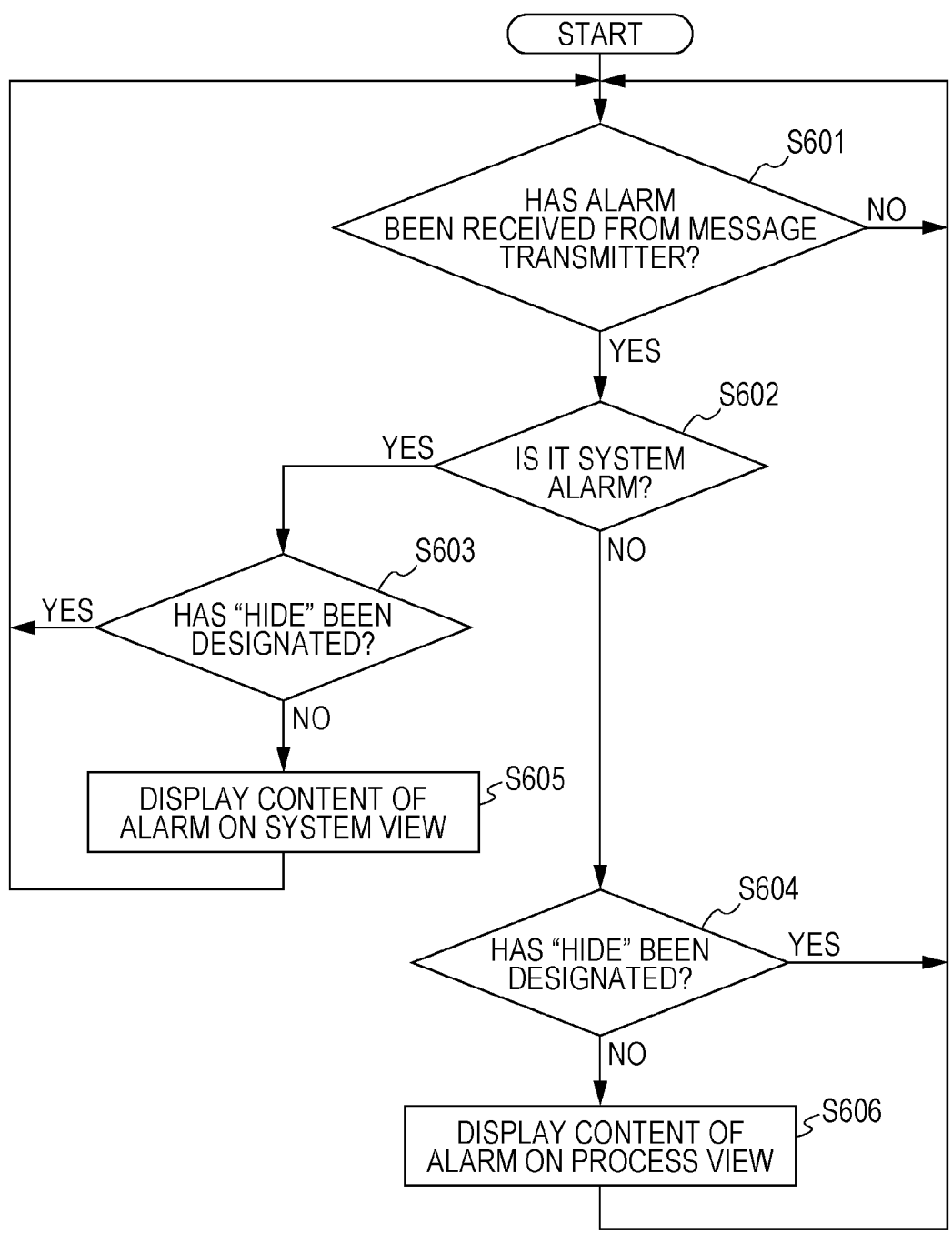
FIG. 6 is a flowchart of an operation monitoring terminal according to one or more embodiments of the invention.

FIG. 6 is a flowchart describing the operation of the operation monitoring terminal 2 of the safety instrumented system 100 according to one or more embodiments.

In step S601, the operation monitoring terminal 2 determines whether or not to have received an alarm signal transmitted from the message transmitter 13 of the control apparatus 1. If having received the signal, the operation monitoring terminal 2 proceeds to step S602. In step S602, if the received alarm signal is a system alarm, the operation monitoring terminal 2 proceeds to step S603. In step S603, the operation monitoring terminal 2 determines whether or not "hide" has been designated for the received alarm signal. If "hide" has been designated, the operation monitoring terminal 2 returns to step S601. In this case, the content of the alarm is not displayed on the screen of the operation monitoring terminal 2. If "hide" has not been designated, the operation monitoring terminal 2 proceeds to step S605. In step S605, the content of the alarm is displayed on the system alarm view 23 of the operation monitoring terminal 2. If the received alarm signal is a process alarm in step S602, the operation monitoring terminal 2 proceeds to step S604. In step S604, the operation monitoring terminal 2 determines whether or not "hide" has been designated for the received alarm signal. If "hide" has been designated, the operation monitoring terminal 2 returns to step S601. In this case, the content of the alarm is not displayed on the screen of the operation monitoring terminal 2. If "hide" has not been designated, the operation monitoring terminal 2 proceeds to step S606. In step S606, the content of the alarm is displayed on the process alarm view 22 of the operation monitoring terminal 2.

Figure 7:
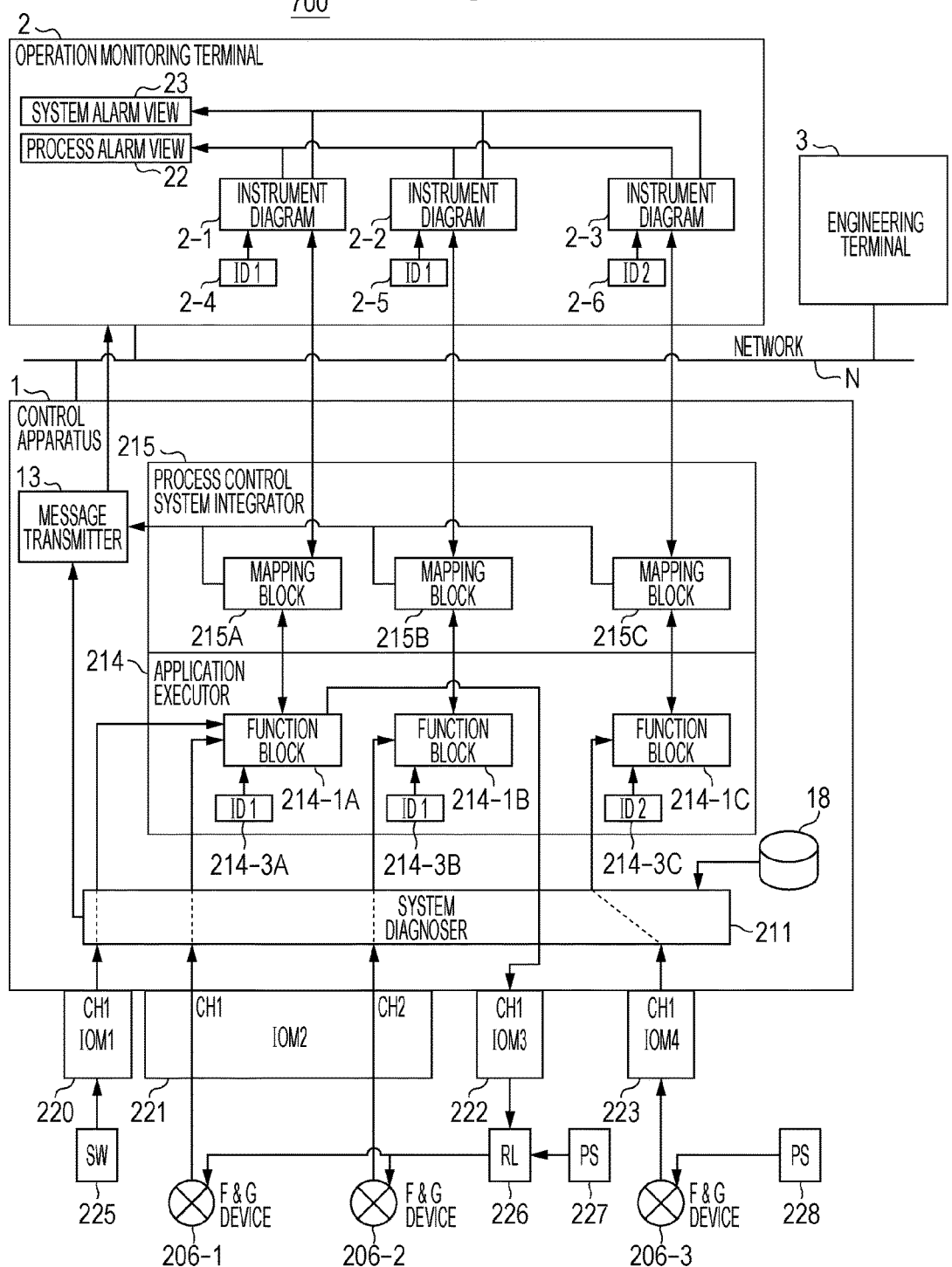
FIG. 7 is a configuration diagram of a safety instrumented system according to one or more embodiments of the invention.

FIG. 7 is a configuration diagram illustrating a safety instrumented system according to one or more embodiments of the invention. As illustrated in FIG. 7, a safety instrumented system 700 mainly includes a control apparatus 1, an operation monitoring terminal 2, an engineering terminal 3, input/output interfaces 220 to 223, and F & G devices 206-1 to 206-3. The control apparatus 1 includes a message transmitter 13, a database 18, a system diagnoser 211, an application executor 214, and a process control system integrator 215. A power supply (PS) 227 supplies power to the F & G devices 206-1 and 206-2 via a relay circuit 226. A power supply (PS) 228 supplies power to the F & G device 206-3.

In one or more embodiments, the operation monitoring terminal 2 has a function of grasping whether or not the F & G devices 206-1 to 206-3 are during reset, according to the reset group IDs. In this case, instrument diagrams 2-1 to 2-3 have timers for grasping whether or not the F & G devices 206-1 to 206-3 are during reset, respectively (not illustrated). Reset group IDs 2-4 to 2-6 and timer count values are preset for the instrument diagrams 2-1 to 2-3 via the engineering terminal 3. When a reset input operation has been performed on a reset input of any of the instrument diagrams 2-1 to 2-3, the timer starts. During a period from the start of the timer to the end of the timer count (that is, during reset), the instrument diagram including the reset input on which the reset input operation has been performed (the instrument diagram where the reset input has been performed) controls a system alarm view 23 or a process alarm view 22 to suppress the display of an alarm corresponding to any of the reset group IDs 2-4 to 2-6 set for the instrument diagram where the reset input has been performed.

Function blocks 214-1A, 214-1B, and 214-1C configure application logic to be executed by the application executor 214 of the control apparatus 1. Reset group IDs 214-3A, 214-3B, and 214-3C are preset by the engineering terminal 3 for the function blocks 214-1A, 214-1B, and 214-1C. The function blocks 214-1A, 214-1B, and 214-1C receive alarm values outputted by the F & G devices 206-1 to 206-3 via the system diagnoser 211 to detect abnormal conditions of the process on the basis of the alarm values. Mapping blocks 215A, 215B, and 215C receive, from the function blocks 214-1A, 214-1B, and 214-1C, the reset group IDs 214-3A, 214-3B, and 214-3C set respectively for the function blocks 214-1A, 214-1B, and 214-1C. The mapping blocks 215A, 215B, and 215C transmit an alarm message that has designated a reset group ID to the operation monitoring terminal 2 via the message transmitter 13.

As in the above-described embodiments, the relationship between information on input/output module identification numbers (IOM) and channel identification numbers (CH), which indicate the mounting locations of the F & G devices 206-1 to 206-3, and the reset group IDs is saved in the database 18 of the control apparatus 1. The relationship is previously defined by using, for example, the engineering terminal 3. The system diagnoser 211 detects abnormal conditions of the system on the basis of alarm values outputted by the F & G devices 206-1 to 206-3. At this point in time, the system diagnoser 211 refers to the database 18, and identifies a reset group ID from the information on the input/output module IOM and the channel CH, which indicate the mounting location of the F & G device that is outputting an alarm value. The system diagnoser 211 transmits the reset group ID and an alarm message to the operation monitoring terminal 2 via the message transmitter 13.

A description is given below of an operation of suppressing an alarm when a reset operation has been inputted into the instrument diagram 2-1. When a reset operation has been inputted into the instrument diagram 2-1, a reset is inputted into the function block 214-1A via the mapping block 215A. The function block 214-1A transmits a reset signal to the relay circuit 226 via the input/output interface 222. Consequently, the relay circuit 226 is activated. Accordingly, the supply of power from the power supply (PS) 227 to the F & G devices 206-1 and 206-2 is interrupted for a fixed amount of time. As a result, the F & G devices 206-1 and 206-2 are reset.

During reset, the F & G devices 206-1 and 206-2 output values different from outputs in their normal operating states. Hence, the system diagnoser 211 detects abnormal conditions of the system. The system diagnoser 211 refers to the relationship between the information on the input/output module identification numbers (IOM) and the channel identification numbers (CH), which indicate the mounting locations of the F & G devices 206-1 and 206-2, and the reset group IDs, the relationship being saved in the database 18. The system diagnoser 211 then identifies the reset group IDs to which the F & G devices 206-1 and 206-2 where the abnormal conditions of the system have been detected belong. The system diagnoser 211 then designates the reset group IDs and transmits an alarm message about the system to the operation monitoring terminal 2 via the message transmitter 13.

The function blocks 214-1A and 214-1B detect abnormal conditions of the process likewise. The mapping blocks 215A and 215B designate the reset group IDs 214-3A and 214-3B set for the function blocks 214-1A and 214-1B, and transmits an alarm message about the process to the operation monitoring terminal 2 via the message transmitter 13.

If a reset operation has been inputted into the instrument diagram 2-1, the timer included in the instrument diagram 2-1 starts counting. The instrument diagram 2-1 sets 1 being the value of the reset group ID 2-4 set for the instrument diagram 2-1 as the reset group ID being a display suppression target, for the system alarm view 23 and the process alarm view 22. During the count of the timer, the system alarm view 23 does not display an alarm message about the system where 1 received from the control apparatus 1 has been designated as the reset group ID. On the other hand, the system alarm view 23 displays an alarm message about the system where a value other than 1 has been designated as the reset group ID. Moreover, the process alarm view 22 does not display an alarm message about the process where 1 received from the control apparatus 1 has been designated as the reset group ID. On the other hand, the process alarm view 22 displays an alarm message about the process where a value other than 1 has been designated as the reset group ID.

When the timer included in the instrument diagram 2-1 finishes the count, the instrument diagram 2-1 cancels the setting of the reset group ID set as the display suppression target for the system alarm view 23 and the process alarm view 22. Consequently, the system alarm view 23 and the process alarm view 22 also display alarm messages about the system where 1 has been designated as the reset group ID.

From the above description, it is possible to appropriately suppress even for an alarm generated due to the reset state of the F & G devices 206-1 and 206-2 from being displayed on the operation monitoring terminal 2.

Next, a description is given of an operation of suppressing an alarm in a case where a reset operation has been inputted into a switch (SW) 225. When a reset operation has been inputted into the switch (SW) 225, a reset is inputted into the function block 214-1A via the system diagnoser 211. The function block 214-1A transmits a reset signal to the relay circuit 226 via the input/output interface 222. Consequently, the relay circuit 226 is activated. Accordingly, the supply of power from the power supply (PS) 227 to the F & G devices 206-1 and 206-2 is interrupted for a fixed amount of time. As a result, the F & G devices 206-1 and 206-2 are reset.

On the other hand, the reset input is transmitted to the instrument diagram 2-1 via the mapping block. Consequently, the timer included in the instrument diagram 2-1 starts. The instrument diagram 2-1 sets 1 being the value of the reset group ID 2-4 set for the instrument diagram 2-1 as the reset group ID being a display suppression target, for the system alarm view 23 and the process alarm view 22.

When the F & G devices 206-1 and 206-2 have been reset, values different from the outputs in the normal operating states are outputted. Hence, the system diagnoser 211 detects abnormal conditions of the system in the F & G devices 206-1 and 206-2. The system diagnoser 211 refers to the relationship between the information on the input/output module identification number (IOM) and the channel identification numbers (CH), which indicate the mounting locations of the F & G devices 206-1 and 206-2, and the reset group IDs, the relationship being saved in the database 18. The system diagnoser 211 identifies the reset group IDs to which the F & G devices 206-1 and 206-2 where the abnormal condition of the system has been detected belong. The system diagnoser 211 then designates the reset group IDs, and transmits an alarm message about the system to the operation monitoring terminal 2 via the message transmitter 13.

The function blocks 214-1A and 214-1B detect abnormal conditions of the process likewise. The mapping blocks 215A and 215B designate the reset group IDs 214-3A and 214-3B set for the function blocks 214-1A and 214-1B and transmit an alarm message about the process to the operation monitoring terminal 2 via the message transmitter 13.

During the count of the timer included in the instrument diagram 2-1, the system alarm view 23 does not display an alarm message about the system where 1 received from the control apparatus 1 has been designated as the reset group ID. On the other hand, the system alarm view 23 displays an alarm message about the system where a value other than 1 has been designated as the reset group ID. Moreover, the process alarm view 22 does not display an alarm message about the process where 1 received from the control apparatus 1 has been designated as the reset group ID. On the other hand, the process alarm view 22 displays an alarm message about the process where a value other than 1 has been designated as the reset group ID.

When the count of the timer included in the instrument diagram 2-1 has ended, the instrument diagram 2-1 cancels the setting of the reset group ID set as a display suppression target for the system alarm view 23 and the process alarm view 22. Consequently, the system alarm view 23 and the process alarm view 22 also display an alarm message about the system where 1 has been designated as the reset group ID.

With the above configuration, it is possible to appropriately suppress even an alarm generated due to the reset state of the F & G devices 206-1 and 206-2 from being displayed on the operation monitoring terminal 2.

As described above, the safety instrumented control apparatus in one or more embodiments transmits an alarm message to the display apparatus on the basis of an output from a field device that continues to output an alarm on the basis of the detection of an abnormal condition until a reset operation is performed. The safety instrumented control apparatus includes the storage, the reset manager, and the diagnoser. A group ID that identifies a group including the field devices, the group ID being predetermined as a target for suppressing the display of an alarm on the display apparatus, is stored in the storage. The reset manager counts on a timer until a predetermined amount of time passes after the reset operation. During the count of the timer for at least any of the field devices belonging to the group ID, the diagnoser adds display suppression information to the alarm message related to the device belonging to the group ID. This configuration enables suppressing an alarm generated by reset of a power supply of the F & G device from being displayed on the operation monitoring terminal. Therefore, it is possible to reduce the confusion of an operator based on the display of a false alarm.

Moreover, as described above, in the safety instrumented control apparatus in one or more embodiments, the display suppression information is information that instructs the display apparatus that displays an alarm message to suppress the display of the alarm message. To suppress the display of the alarm message includes not to display the alarm message or to display the alarm message in a form different from a normal form. Consequently, it is possible to suppress an alarm generated by reset of a power supply of an F & G device from being displayed on the operation monitoring terminal. Therefore, it is possible to reduce the confusion of the operator based on the display of a false alarm.

As described above, the safety instrumented control apparatus in one or more embodiments includes the resetter that transmits a reset command to the input/output module. The resetter identifies information on a channel connected to the field devices on the basis of the reset operation, and transmits a reset command through the channel identified from the reset identification information by referring to the definition information. Consequently, it is possible to suppress an alarm generated by reset of a power supply of the F & G device from being displayed on the operation monitoring terminal. Therefore, it becomes possible to reduce the confusion of the operator based on the display of a false alarm.

One or more embodiments of the invention may be the following one to ninth safety instrumented control apparatuses, first and second safety instrumented systems, and first and second plant control methods.

The first safety instrumented control apparatus is characterized by including, in a safety instrumented control apparatus that transmits an alarm message to a display apparatus on the basis of an output from a field device that continues to output an alarm on the basis of detection of an abnormal condition until a reset operation is performed: a storage configured to store a group ID for identifying a group including the field devices predetermined as targets for suppressing the display of an alarm on the display apparatus; a reset manager configured to count on a timer until a predetermined amount of time passes after the reset operation; and a diagnoser configured to, during the count of the timer for at least any of the field devices belonging to the group ID, add display suppression information to the alarm message related to the device belonging to the group ID and suppress the display of an alarm on the basis of the information.

The second safety instrumented control apparatus is the first safety instrumented control apparatus, and is characterized in that the storage stores definition information where information on channels connected to the field devices in input/output modules connected to the control apparatus itself is associated with the group IDs, and, the diagnoser refers to the definition information on the basis of the channel information of the input/output module that has received an output from the field device, and identifies the group ID to which the field device targeted for the reset operation belongs.

The third safety instrumented control apparatus is the first or second safety instrumented control apparatus, and is characterized in that the diagnoser includes a process alarm diagnoser configured to detect an abnormal condition in process control being a controlled target of the control apparatus itself on the basis of an output value of the field device, and transmit a process alarm as an alarm message to be displayed on the display apparatus.

The fourth safety instrumented control apparatus is any one of the first to third safety instrumented control apparatuses, and is characterized in that the diagnoser includes a system diagnoser configured to diagnose at least any of the states of the control apparatus itself, the input/output module, and the field devices, and their connection states, detect an abnormal condition of a system, and transmit a system alarm as an alarm message to be displayed on the display apparatus.

The fifth safety instrumented control apparatus is any one of the first to fourth safety instrumented control apparatuses, and is characterized in that to suppress the display of the alarm message includes not to display the alarm message, or to display the alarm message in a form different from a normal form.

The sixth safety instrumented control apparatus is the fifth safety instrumented control apparatus, and not to display the alarm message includes to suppress the control apparatus from detecting an alarm during the count of the timer, or to suppress the control apparatus from transmitting an alarm during the count of the timer.

The seventh safety instrumented control apparatus is any one of the first to sixth safety instrumented control apparatuses, and is characterized in that the storage stores the definition information where reset identification information for identifying at least one or more field devices targeted for the reset operation is associated with the group ID, and the reset manager refers to the definition information on the basis of the reset operation, identifies the group ID from the reset identification information, and starts counting on a timer for the group ID.

The eighth safety instrumented control apparatus is any one of the first to seventh safety instrumented control apparatuses, includes a resetter configured to transmit a reset command to the input/output module, and is characterized in that the resetter identifies information on a channel connected to the field device on the basis of the reset operation, the definition information, and the reset identification information, and transmits a reset command through the identified channel.

The ninth safety instrumented control apparatus is any one of the first to eighth safety instrumented control apparatuses, includes: a record holder where an alarm is saved irrespective of whether or not during reset; and an activation state manager configured to manage an activation state of the field device, and is characterized in that when the activation state manager finds that any of the field devices has not yet returned to normal after the end of the count of the timer, the diagnoser retransmits an alarm during reset saved in the record holder to the display apparatus.

The first safety instrumented system is characterized by including: any one of the first to seventh safety instrumented control apparatuses; and an engineering terminal configured to previously define group IDs for identifying groups including the field devices predetermined as targets for suppressing the display of an alarm on the display apparatus and/or definition information where information on channels connected to the field devices in input/output modules connected to the safety instrumented control apparatus is associated with the group IDs, and download the group IDs and/or the definition information to a storage of the control apparatus.

The second safety instrumented system is the first safety instrumented system, and is characterized by including: the safety instrumented control apparatus; and a display apparatus configured to receive an alarm message transmitted from the safety instrumented control apparatus via a network, suppress the display of the alarm message upon display suppression information having been added to the alarm message, and display the alarm message upon the display suppression information having not been added to the alarm message.

The first plant control method includes, in a plant control method that transmits an alarm message to a display apparatus on the basis of an output from a field device that continues to output an alarm on the basis of detection of an abnormal condition until a reset operation is performed, the steps of: storing a group ID for identifying a group including the field devices predetermined as targets for suppressing the display of an alarm on the display apparatus; counting on a timer until a predetermined amount of time passes after the reset operation; and, during the count of the timer for at least any of the field devices belonging to the group ID, adding display suppression information to the alarm message related to the device belonging to the group ID.

The second plant control method is the first plant control method, and is characterized by further including the steps of: storing definition information where information on channels connected to the field devices in input/output modules connected to the control apparatus is associated with the group IDs; and referring to the definition information on the basis of the channel information of the input/output module that has received an output from the field device, and identifying the group ID to which the field device targeted for the reset operation belongs.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A safety instrumented control apparatus comprising:
   a message transmitter that transmits an alarm message to a display apparatus based on an output from a field device that continues to output an alarm upon detecting an abnormal condition until a reset operation is performed;
   a storage that stores a group ID for identifying a group of the field devices;
   a reset circuit that counts on a timer until a predetermined amount of time passes after the reset operation;
   a diagnosing circuit that, during the count of the timer for any of the field devices belonging to the group ID, adds display suppression information to the alarm message related to the field device belonging to the group ID;
   a record storage where the alarm message is saved irrespective of the count of the timer; and
   an activation state managing circuit that manages an activation state of the field device, wherein
   when any one of the field devices has not returned to a normal state after the end of the count of the timer, the diagnosing circuit retransmits, to the display apparatus, the alarm message during the count of the timer saved in the record storage.

2. The safety instrumented control apparatus according to claim 1, wherein
   the storage stores definition information where information on channels connected to the field devices in input/output modules connected to the safety instrumented control apparatus is associated with the group IDs, and
   the diagnosing circuit refers to the definition information based on channel information of the input/output module that has received an output from the field device, and identifies the group ID to which the field device targeted for the reset operation belongs.

3. The safety instrumented control apparatus according to claim 1, wherein
the diagnosing circuit comprises a process alarm diagnosing circuit, and
the process alarm diagnosing circuit detects an abnormal condition in process control being a controlled target of the safety instrumented control apparatus based on an output value of the field device, and transmits a process alarm as the alarm message to be displayed on the display apparatus.

4. The safety instrumented control apparatus according to claim 2, wherein
the diagnosing circuit comprises a system diagnosing circuit, and
the system diagnosing circuit diagnoses at least any of states of the safety instrumented control apparatus, the input/output module, and the field device, and their connection states based on the output from the field device, detects an abnormal condition of a system, and transmits a system alarm as the alarm message to be displayed on the display apparatus.

5. The safety instrumented control apparatus according to claim 1, wherein
the display suppression information instructs the display apparatus to suppress the display of the alarm message, and
suppressing the display of the alarm message includes not displaying the alarm message, or displaying the alarm message in a form different from a normal form.

6. The safety instrumented control apparatus according to claim 1, wherein the diagnosing circuit suppresses the detection of the abnormal condition, or to suppress the transmission of the alarm message, during the count of the timer.

7. The safety instrumented control apparatus according to claim 2, wherein
the storage stores, as the definition information, information where reset identification information for identifying at least one or more field devices targeted for the reset operation is associated with the group ID, and
the reset circuit refers to the definition information based on the reset operation, identifies the group ID from the reset identification information, and starts counting on the timer for the group ID.

8. The safety instrumented control apparatus according to claim 7, further comprising
a resetting circuit that transmits a reset command to the input/output module, wherein
the resetting circuit identifies information on a channel connected to the field device based on the reset operation, the definition information, and the reset identification information, and transmits a reset command based on the identified channel information.

9. A safety instrumented system comprising:
the safety instrumented control apparatus according to claim 1; and
an engineering terminal that previously defines group IDs for identifying groups including the field devices predetermined as targets for suppressing the display of an alarm on the display apparatus and/or definition information where information on channels connected to the field devices in input/output modules connected to the safety instrumented control apparatus is associated with the group IDs, and downloads the group IDs and/or the definition information to the storage of the safety instrumented control apparatus.

10. The safety instrumented system according to claim 9, further comprising
a display apparatus that receives an alarm message transmitted from the safety instrumented control apparatus via a network, suppresses the display of the alarm message upon display suppression information having been added to the alarm message, and displays the alarm message upon the display suppression information having not been added to the alarm message.

11. A plant control method comprising:
transmitting an alarm message to a display apparatus based on an output from a field device that continues to output an alarm upon detection of an abnormal condition until a reset operation is performed;
storing a group ID for identifying a group of the field devices;
counting on a timer until a predetermined amount of time passes after the reset operation;
during the count of the timer for any of the field devices belonging to the group ID, adding display suppression information to the alarm message related to the field device belonging to the group ID;
saving the alarm message irrespective of the count of the timer;
managing an activation state of the field device; and
when any one of the field devices has not returned to a normal state after the end of the count of the timer, retransmitting, to the display apparatus, the alarm message during the count of the timer saved in the record storage.

12. The plant control method according to claim 11, further comprising:
storing definition information where information on channels connected to the field devices in input/output modules is associated with the group IDs; and
referring to the definition information based on the channel information of the input/output module that has received an output from the field device, and identifying the group ID to which a field device targeted for the reset operation belongs.

13. A safety instrumented control apparatus comprising:
a message transmitter that transmits an alarm message to a display apparatus based on an output from a field device that continues to output an alarm upon detecting an abnormal condition until a reset operation is performed;
a storage that stores, as definition information, information where a group ID for identifying a group of the field devices, a reset variable, and an ID of an input/output module connected to the safety instrumented control apparatus are associated with one another;
an application executing circuit that outputs, in response to the reset operation, a reset signal to the reset variable;
a resetting circuit that refers to the definition information and transmits a reset command to the input/output module corresponding to the reset variable;
a reset circuit that counts on a timer until a predetermined amount of time passes after the reset operation; and
a diagnosing circuit that, during the count of the timer for any of the field devices belonging to the group ID corresponding to the reset variable, adds display suppression information to the alarm message related to the field device belonging to the group ID.

* * * * *